United States Patent

Wadhwa et al.

(10) Patent No.: US 10,520,492 B2
(45) Date of Patent: Dec. 31, 2019

(54) METHOD OF SCREENING FOR CANDIDATE COMPOUNDS FOR REGULATING MELANOGENESIS OR PIGMENTATION

(71) Applicants: CHANEL PARFUMS BEAUTE, Neuilly sur Seine (FR); NATIONAL INSTITUTE OF ADVANCED INDUSTRIAL SCIENCE AND TECHNOLOGY, Tokyo (JP)

(72) Inventors: Renu Wadhwa, Tsuchiura (JP); Sunil Kaul, Tsuchiura (JP); Nobuhiro Ando, Tokyo (JP); Christian Mahe, Neuilly sur Seine (FR)

(73) Assignees: CHANEL PARFUMS BEAUTE, Neuilly sur Seine (FR); NATIONAL INSTITUTE OF ADVANCED INDUSTRIAL SCIENCE AND TECHNOLOGY, Tokyo (JP)

( * ) Notice: Subject to any disclaimer, the term of this patent is extended or adjusted under 35 U.S.C. 154(b) by 379 days.

(21) Appl. No.: 14/786,475

(22) PCT Filed: Apr. 29, 2014

(86) PCT No.: PCT/EP2014/058697
§ 371 (c)(1),
(2) Date: Oct. 22, 2015

(87) PCT Pub. No.: WO2014/177550
PCT Pub. Date: Nov. 6, 2014

(65) Prior Publication Data
US 2016/0153968 A1    Jun. 2, 2016

(30) Foreign Application Priority Data

Apr. 30, 2013 (JP) ................................ 2013-095829

(51) Int. Cl.
*G01N 31/00*    (2006.01)
*G01N 33/53*    (2006.01)
*G01N 33/50*    (2006.01)
*A61K 8/60*     (2006.01)
*A61K 31/7105*  (2006.01)
*A61Q 19/02*    (2006.01)

(52) U.S. Cl.
CPC .......... *G01N 33/5044* (2013.01); *A61K 8/60* (2013.01); *A61K 31/7105* (2013.01); *A61Q 19/02* (2013.01); *G01N 2500/10* (2013.01); *G01N 2800/207* (2013.01)

(58) Field of Classification Search
None
See application file for complete search history.

(56) References Cited

U.S. PATENT DOCUMENTS

2002/0034772 A1    3/2002  Orlow et al.

OTHER PUBLICATIONS

Aoki et al. (Biosci. Biotechnol. Biochem., vol. 71, No. 8, pp. 1879-1885, 2007).*
Carta et al. (Melanoma Research, 2005, vol. 15, pp. 235-244).*
Lee et al. Eur Journal Immunology, 2011, 41, pp. 2937-2946.*
Francesco Cappello et al: "Hsp60 expression, new locations, functions, and perspectives for cancer diagnosis and therapy", Cancer Biology & Therapy, vol. 7, No. 6, Jun. 1, 2008 (Jun. 1, 2008), pp. 801-809, XP055132679, ISSN: 1538-4047, DOI: 10.4161/cbt.7.6.6281.
Carta F et al: "Analysis of candidate genes through a proteomics-based approach in primary cell lines from malignant melanomas and their metastases", Melanoma Research, Lippincott Williams & Wilkins, US, vol. 15, No. 4, Aug. 1, 2005 (Aug. 1, 2005), pp. 235-244, XP008096548, ISSN: 0960-8931, DOI: 10.1097/00008390-200508000-00002.
Ji H. Lee et al: "1,25-Dihydroxyvitamin D3 enhances NK susceptibility of human melanoma cells via Hsp60-mediated FAS expression", European Journal of Immunology, vol. 41, No. 10, Oct. 6, 2011 (Oct. 6, 2011), pp. 2937-2946, XP055132670, ISSN: 0014-2980, DOI: 10.1002/eji.201141597.
Deocaris Custer C et al: "The versatile stress protein mortalin as a chaperone therapeutic agent", Protein and Peptide Letters, Bentham Science Publ, NL, vol. 16, No. 5, Jan. 1, 2009 (Jan. 1, 2009), pp. 517-529, XP009179450, ISSN: 1875-5305.
Anonymous: "Herbal Cananga Oil Relaxing and Whitening Body Wash—Buy Body Wash,Whitening Skin Body Wash Product on Alibaba.com",Jan. 1, 2014 (Jan. 1, 2014), XP055133221, Retrieved from the Internet: URL:http://www.alibaba.com/product-detail/Herbal-Cananga-Oil-Relaxing-and-Whitening_1941163341.html [retrieved on Aug. 5, 2014].
Tradesparq.Com: "Plum Blossom Whitening Facial Mask: China Suppliers—1314192",Jan. 1, 2014 (Jan. 1, 2014), XP055133224, Retrieved from the Internet: URL:http://www.tradesparq.com/products/1314192/Plum-Blossom-Whitening-Facial-Mask-manufacturers [retrieved on Aug. 5, 2014].
"Anti-glycation ingredient for skin and hair", Apr. 11, 2013 (Apr. 11, 2013), XP055132748, Retrieved from the Internet: URL:http://www.cosmesi.it/Portals/7/Documenti/Ume Extract (B)-BG_Presentation.pdf [retrieved on Jul. 31, 2014].
Yumi Aoki et al: "Melanogenesis Inhibition by an Oolong Tea Extract in B16 Mouse Melanoma Cells and UV-Induced Skin Pigmentation in Brownish Guinea Pigs", Bioscience, Biotechnology, and Biochemistry, vol. 71, No. 8, Aug. 23, 2007 (Aug. 23, 2007), pp. 1879-1885, XP055132753, ISSN: 0916-8451, DOI: 10.1271/bbb.70099.
International Search Report, dated Aug. 13, 2014, from corresponding PCT Application.

* cited by examiner

*Primary Examiner* — Lisa V Cook
(74) *Attorney, Agent, or Firm* — Young & Thompson

(57) ABSTRACT

A method to identify target genes or proteins for regulating melanogenesis or pigmentation and to screen for compounds for manipulation of melanogenesis or pigmentation, the method of screening for candidate compounds for regulating melanogenesis or pigmentation, includes bringing test compounds into contact with cells capable of expressing mortalin and/or Hsp60 in vitro, and selecting, from among the test compounds, a compound that changes the expression level of mortalin and/or Hsp60.

3 Claims, 12 Drawing Sheets

Specification includes a Sequence Listing.

G361 cells/OAG-treated

SEQUENCE LISTING

```
<160> NUMBER OF SEQ ID NOS: 7

<210> SEQ ID NO 1
<211> LENGTH: 19
<212> TYPE: DNA
<213> ORGANISM: Homo sapiens
<220> FEATURE:
<221> NAME/KEY: misc_feature
<223> OTHER INFORMATION: Target sequence of shRNA against mortalin.

<400> SEQUENCE: 1
gcaacaagct gaaagaaga                                                   19

<210> SEQ ID NO 2
<211> LENGTH: 19
<212> TYPE: DNA
<213> ORGANISM: Homo sapiens
<220> FEATURE:
<221> NAME/KEY: misc_feature
<223> OTHER INFORMATION: Target sequence of shRNA against mortalin.

<400> SEQUENCE: 2
gccagaagga caacatatg                                                   19

<210> SEQ ID NO 3
<211> LENGTH: 19
<212> TYPE: DNA
<213> ORGANISM: Homo sapiens
<220> FEATURE:
<221> NAME/KEY: misc_feature
<223> OTHER INFORMATION: Target sequence of shRNA against mortalin.
```

```
<400> SEQUENCE: 3
gaatgaggct agaccttta                                              19

<210> SEQ ID NO 4
<211> LENGTH: 64
<212> TYPE: DNA
<213> ORGANISM: Artificial
<220> FEATURE:
<223> OTHER INFORMATION: Sense sequence of shRNA against mortalin.

<400> SEQUENCE: 4
gatcccgcaa caagctgaaa gaagattcaa gagatcttct ttcagcttgt tgcttttttg    60
gaaa                                                               64

<210> SEQ ID NO 5
<211> LENGTH: 64
<212> TYPE: DNA
<213> ORGANISM: Artificial
<220> FEATURE:
<223> OTHER INFORMATION: Antisense sequence of shRNA against mortalin.

<400> SEQUENCE: 5
agcttttcca aaaagcaac aagctgaaag aagattcaag agatcttctt tcagcttgtt    60
gcgg                                                               64

<210> SEQ ID NO 6
<211> LENGTH: 21
<212> TYPE: DNA
<213> ORGANISM: Homo sapiens
<220> FEATURE:
<221> NAME/KEY: misc_feature
<223> OTHER INFORMATION: Target sequence of shRNA against HSP60.

<400> SEQUENCE: 6
gtgagatgag gagccagtac c                                            21

<210> SEQ ID NO 7
<211> LENGTH: 21
<212> TYPE: DNA
<213> ORGANISM: Homo sapiens
<220> FEATURE:
<221> NAME/KEY: misc_feature
<223> OTHER INFORMATION: Target sequence of shRNA against mortalin.

<400> SEQUENCE: 7
ttcaagcatt aaggctcggg c                                            21
```

METHOD OF SCREENING FOR CANDIDATE COMPOUNDS FOR REGULATING MELANOGENESIS OR PIGMENTATION

The present application is a 371 of International Application PCT/EP2014/058697 filed Apr. 29, 2014, which claimed priority to Japanese Application No. 2013-095829 filed Apr. 30, 2013.

TECHNICAL FIELD

The present invention relates to a screening method for candidate compounds for regulating melanogenesis or pigmentation.

BACKGROUND ART

Melanogenesis is a process through which special melanin-producing cells, called melanocytes, produce melanin pigment. Melanocytes constitute 5% to 10% of cells in the basal layer of the epidermis. There are typically 1000 to 2000 melanocytes per square millimeter of skin. Although variable in size, melanocytes are typically seven micrometers in length.

Melanin levels vary across different human populations varying from lightly to darkly pigmented individuals, depending on the level of activity of melanocytes and the quantity of eumelanin and pheomelanin they produce. This process is regulated by the tyrosinase enzyme, which is required for melanocytes to produce melanin from the amino acid tyrosine, and is highly influenced by hormones, including the MSH and ACTH peptides that are produced from the precursor proopiomelanocortin. A low level of melanogenesis is stimulated by exposure to UV-B radiation.

Once synthesized, Melanin is stored in special structures called melanosomes. The melanosomes are shipped to the top layer of keratinocytes along arm-like structures called dendrites. Melanin plays an important role there in protection of skin from UV-induced damage. Individuals having low levels of endogenous pigmentation tend to have a high incidence of skin cancers and, hence, agents that induce melanogenesis hold potential as protective agents for UV-induced skin damage and carcinogenesis. Furthermore, chemical agents that induce pigmentation could also serve as differentiating agents for skin cancers. On the other hand, agents that induce depigmentation are valuable for treatment of moles, dark spots that appear on aging skin or specific skin conditions, such as keloids or post-inflammatory hyperpigmentation and skin whitening as desired in cosmetics. Melanogenesis is a complex process that remains incompletely understood. It warrants studies on the identification of cellular factors involved in this process and approaches for its safe and functional manipulation.

There is thus a need for an identification of target genes or proteins for regulating melanogenesis or pigmentation and for providing a screening method for compounds acting on melanogenesis or pigmentation.

PRIOR ART DOCUMENTS

1. Chiang H M, Lin J W, Hsiao P L, Tsai S Y, Wen K C. Hydrolysates of citrus plants stimulate melanogenesis protecting against UV-induced dermal damage. Phytother Res 2010; 25: 569-76.
2. Kimura Y, Sumiyoshi M. French maritime pine bark (*Pinus maritima* Lam.) extract (Flavangenol) prevents chronic UVB radiation-induced skin damage and carcinogenesis in melanin-possessing hairless mice. Photochem Photobiol 2010; 86: 955-63.
3. Gidanian S, Mentelle M, Meyskens F L, Jr., Farmer P J. Melanosomal damage in normal human melanocytes induced by UVB and metal uptake—a basis for the prooxidant state of melanoma. Photochem Photobiol 2008; 84: 556-64.
4. Costin G E, Hearing V J. Human skin pigmentation: melanocytes modulate skin color in response to stress. Faseb J 2007; 21: 976-94
5. Seo Y K, Kim S J, Boo Y C, Baek J H, Lee S H, Koh J S. Effects of p-coumaric acid on erythema and pigmentation of human skin exposed to ultraviolet radiation. Clin Exp Dermatol 2011; 36: 260-6.

SUMMARY OF THE INVENTION

An object of the present invention is to provide a screening method for compounds regulating melanogenesis or pigmentation.

The present inventors have carried out an extensive investigation to solve the above-mentioned problem. As a result, the inventors have demonstrated that mortalin and Hsp60 are involved in skin pigmentation. More specifically, the inventors have revealed that a high expression level of mortalin or Hsp60 results in an increase of melanogenesis or pigmentation, and an inhibition of expression or activity of mortalin or Hsp60 leads to depigmentation or whitening of skin.

The present invention is thus related to a method of screening for candidate compounds for regulating melanogenesis or pigmentation, comprising:
(i) bringing test compounds into contact with cells capable of expressing mortalin and/or Hsp60, and
(ii) selecting, from among the test compounds, a compound that changes the expression level of Mortalin and/or Hsp60.

The present invention is also related to a method of screening for candidate compounds for skin depigmentation, skin whitening, or inhibition of melanogenesis, comprising:
(i) bringing test compounds into contact with cells capable of expressing mortalin and/or Hsp60, and
(ii) selecting, from among the test compounds, a compound that decreases the expression level of Mortalin and/or Hsp60.

The present invention is also related to a method of screening for candidate compounds for inducing melanogenesis or skin pigmentation, comprising:
(i) bringing test compounds into contact with cells capable of expressing Mortalin and/or Hsp60, and
(ii) selecting, from among the test compounds, a compound that increases the expression level of Mortalin and/or Hsp60.

All the methods of the invention are in vitro methods.

The above described methods according to the invention preferably further comprise a step of inducing melanogenesis and/or pigmentation in the cells, before step (i) (i.e. bringing the test compounds into contact with said cells).

Preferably, the expression level of mortalin and/or Hsp60 is determined by ELISA. Preferably, the cells capable of expressing mortalin and/or Hsp60 are chosen from human melanoma cells and melanocytes.

The present invention also relates to a pharmaceutical composition, preferably for inducing pigmentation or melanogenesis, comprising an expression vector containing an Hsp60 gene and/or mortalin gene, or an Hsp60 protein and/or mortalin protein. Said pharmaceutical composition is preferably used for the treatment of skin disorders. Preferably, the skin disorder is selected from the group consisting of cancer, hyperpigmentation, rash and keloids.

The present invention is also related to a method for modulating pigmentation or melanogenesis, comprising manipulating mitochondrial functions based on mortalin, HSP60 and other proteins in mitochondria. The present invention is also related to a method for modulating pigmentation or melanogenesis, comprising manipulating oxidative stress response of cells that involves mortalin, HSP60 and other proteins in mitochondria.

The present invention is also related to the cosmetic use of an inhibitor of the expression of at least one gene selected from mortalin and Hsp60, which can be obtained according to the screening method of the invention, for whitening the skin.

The present invention also describes a method for controlling melanogenesis or pigmentation in cultured skin cells, comprising:
    differentiating stem cells into skin cells in vitro, and
    regulating the amount of mortalin and/or Hsp60 in the cultured skin cells.

By the screening method of the present invention, candidate compounds (also called "test compounds") for regulating melanogenesis or pigmentation are selected. Preferably, said candidate compounds are for skin depigmentation, skin whitening or inhibition of melanogenesis. Said selected compounds for skin depigmentation, skin whitening or inhibition of melanogenesis could be used as a drug for treating moles, keloids, or hyperpigmentation, or as a whitening agent in cosmetics.

Alternatively, said candidate compounds are for inducing skin pigmentation or melanogenesis. Said selected compounds for inducing melanogenesis or skin pigmentation could be used as a protective agent for UV-induced skin damage or carcinogenesis, or for treating skin cancers.

The pharmaceutical composition of the present invention preferably induces skin pigmentation or melanogenesis through activation of tyrosinase.

According to the method for controlling the melanogenesis or pigmentation of the present invention, the color of cultured skin used for transplantation can be appropriately regulated.

BRIEF DESCRIPTION OF THE DRAWINGS

FIG. 16 shows G361 cells treated with OAG (30 μg/ml) followed by their recovery in the absence (control) or presence of either of the 3 drugs (indicated by numbers), selected on the basis of the screening method, shown in FIG. 14. Actin was used as an internal loading control.

FIG. 17 shows G361 cells treated with OAG followed by their recovery in the absence (control) or presence of either of the 3 drugs (indicated by numbers), selected on the basis of the screening method, shown in FIG. 14.

FIG. 18 shows primary melanocytes derived from human white skin treated with OAG (15 μg/ml).

FIG. 19 shows human white skin-derived primary melanocytes treated with OAG (15 μg/ml) and the melanin content.

MODE FOR CARRYING OUT THE INVENTION

Screening Method

Figure 1:
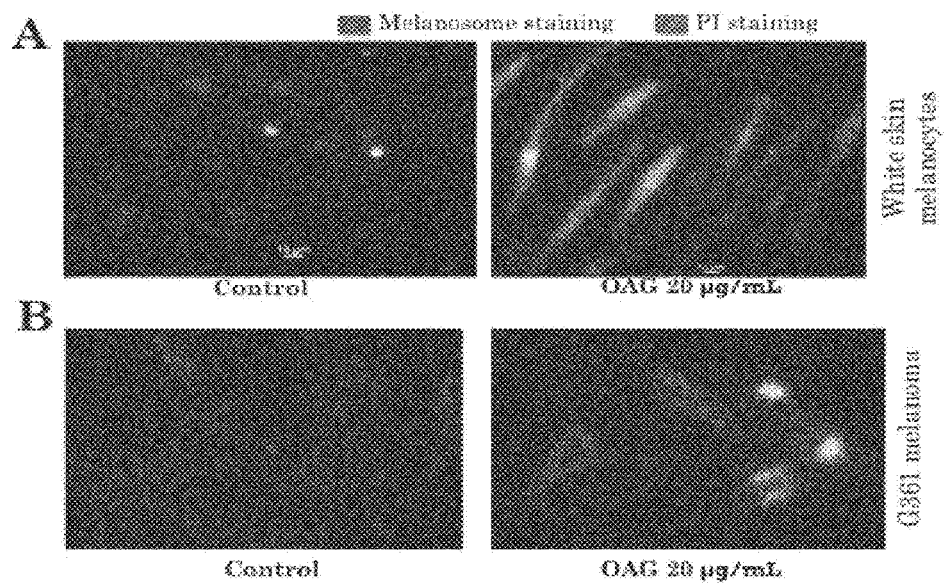
FIG. 1 shows the results of an immunohistochemistry analysis of melanosome induction in control and OAG-treated primary melanocytes from a white skin donor (A) and human melanoma cells G361 (B).

The in vitro screening method of the present invention is a method of screening for candidate compounds (also called "test compounds") for regulating melanogenesis or pigmentation, comprising: (i) bringing test compounds into contact with cells capable of expressing mortalin and/or Hsp60, and (ii) selecting, from the test compounds, a compound that changes the expression level of mortalin and/or Hsp60. Preferably, in step (ii), any compound changing the expression level of mortalin and/or Hsp60 of at least 20% is selected.

The term "melanogenesis" as used herein, means a process through which melanin is produced in melanocytes. As described above, tyrosinase is required for the melanogenesis to take place. Tyrosinase oxidizes tyrosine in the melanocytes to produce phenols which are further oxidized enzymatically or non-enzymatically, decarboxylated, and polymerized to produce melanin, a brownish or black pigment. Once produced, melanin is stored in a cell organelle called a melanosome, transported to a top layer of keratinocytes, and then protects DNA in a cell nucleus from ultraviolet damage.

The term "pigmentation" as used herein means a process through which melanin is accumulated excessively and the skin is colored.

The term "regulating melanogenesis or pigmentation" as used herein, means promoting or inhibiting melanogenesis or skin pigmentation. In other words, the regulation of melanogenesis or pigmentation includes inducing melanogenesis inhibition, depigmentation, or whitening, as well as inducing melanogenesis or pigmentation.

The term "candidate compound" as used herein, means any substance that can be used in the screening method of the present invention. Examples of candidate compounds include, but are not limited to, nucleic acids, peptides, proteins, sugars, lipids, small molecules, plant extracts or polymers.

"Mortalin" as used herein, means a protein, also termed as mitochondria heat shock protein 70 (mthsp70), peptide binding protein 74 (PBP74), or glucose regulated protein 75 (Grp75). It is a member of the Hsp70 chaperone family of proteins and has been shown to possess unique functional characteristics in a number of different subcellular loci. The functional roles of mortalin can be classified into two major classes based upon its subcellular location. The first class of functions involves those that occur in the mitochondrion and includes its participation in the import of nuclear-encoded proteins into the mitochondrion, nascent protein folding, protein degradation within the mitochondrion, and interaction with submitochondrial constituents to maintain its integrity and functions. The second class of functions involves its extra-mitochondrial roles that include its interaction with and functional regulation of several cytoplasmic, endoplasmic-reticulum and nuclear proteins, centrosomes, growth factors, immune system constituents, and metabolic constituents (Wadhwa R et al., J Biol Chem 1993; 268: 6615-21; Wadhwa R et al., J Biol Chem 1998; 273: 29586-91; Wadhwa R et al., Cancer Res 2000; 60: 6818-21; Kaul S C et al., J Biol Chem 2005; Kanai M et al., Genes Cells 2007; 12: 797-810; Ma Z et al., Oncogene 2006; 25: 5377-5390; Lu W J et al., Cell Death Differ 2011; 18: 1046-56; Pilzer D et al., Int Immunol 2005; 17: 1239-48).

Mortalin is frequently enriched in human cancers and has been functionally related to human carcinogenesis (Cussac et al. 2006; Dundas et al. 2005; Ma et al. 2006; Shin et al. 2003; Wadhwa et al. 2006; Lu et al. 2011, Yi et al. 2008). Cancer cells with higher levels of mortalin expression show enhanced malignant properties, including anchorage-independent growth, formation of tumors in nude mice and chemotaxis. Quantitative estimation of protein expression reveal that the tumors that express high levels of mortalin have more aggressive malignant phenotypes, including tumor volume and metastasis (Dundas et al. 2005; Lu et al. 2011). Furthermore, levels of mortalin expression in tumor tissues positively correlate with poor patient survival (Dundas et al. 2005) and tumor reoccurrence after surgery (Yi et al. 2008).

Forced overexpression of mortalin in normal human fibroblasts results in their extended lifespan (Kaul et al. 2001; Wadhwa et al. 1998; Wadhwa et al. 2002c). Besides cancers, mortalin has been reported to play a role in neuronal functions including neuronal differentiation (Shin et al. 2012), obesity (Olivia et al. 2012) and NFk-B signaling (Li et al. 2010). Consistent with the concept that mitochondrial dysfunction is involved in the pathogenesis of several major neurological diseases, including neurodegenerative disorders (Alzheimer's disease, Parkinson's disease) and cerebral ischemia, mortalin dysfunction has been shown to be involved in such diseases.

Heat shock protein 60 (Hsp60) is another mitochondrial stress protein that has been shown to be involved in protein assembly and folding (Soltys and Gupta, 1997) as well as in cellular stress response (Gupta and Knowlton, 2002). Similar to mortalin, Hsp60 has been found in mitochondria and extra-mitochondrial sites (Soltys and Gupta, 1996; Cechetto et al. 2000, Cicconi et al. 2004), and is up-regulated in many kinds of tumors (Cappello et al., 2003; Pignatelli et al, 2003). Furthermore, mortalin and Hsp60 have been shown to exist in a complex and to contribute to carcinogenesis (Wadhwa et al. 2005).

"Mortalin" or "Hsp60" as used herein, include naturally-occurring or artificial mutants, insofar as they have the functionality of inducing melanogenesis or pigmentation. Such mutants may include, for example, polypeptides comprising an amino acid sequence with 90% or more identity to that of wild-type mortalin or wild-type Hsp60, and having melanogenesis- or pigmentation-inducing ability. A person skilled in the art could easily identify whether a mutant protein has melanogenesis- or pigmentation-inducing ability according to any known method, such as that described in the Examples of the present application.

The term "cells capable of expressing mortalin and/or Hsp60" as used herein, refers to cells that can express at least one of mortalin and Hsp 60 constantly or transiently.

The term "expression" as used herein, includes both transcription through which an mRNA is synthesized based on the sequence of a template DNA and translation through which a protein is synthesized by a tRNA that sequentially decodes an mRNA. Examples of the cells capable of expressing mortalin and/or Hsp60 include a melanocyte and a melanoma cell. A melanocyte is a cell that contains tyrosinase and generates melanin from tyrosine. Melanoma is a malignant tumor that develops in melanocytes. Melanoma cells include, but are not limited to, mouse melanoma B16 cells, human melanoma SK-MEL-28 cells, and human melanoma G361 cells. These cells can be cultured by known methods.

The cells capable of expressing mortalin and/or Hsp60 in the present application are not necessarily the cells that produce melanin.

Preferably, the cells capable of expressing mortalin and/or Hsp60 are chosen from human melanoma cells and melanocytes.

The step (i) of bringing test compounds into contact with cells capable of expressing mortalin and/or Hsp60 can be appropriately performed by a person skilled in the art. For example, such step can be performed by adding a test compound into the culture medium of the cells capable of expressing mortalin and/or Hsp60 at an appropriate concentration.

The step (ii) of selecting, from among the test compounds, a compound that changes the expression level of mortalin and/or Hsp60, can be performed by, for example, determining the expression level of mortalin and/or Hsp60 at multiple time points before and after the contact of the cells and the test compound, and comparing the expression levels of at least two time points. Preferably, the selected compounds change the expression level of mortalin and/or Hsp60 of at least 20%, preferably at least 30%, more preferably at least 50%.

Thus, step (ii) includes:

(iiA) determining the expression level of mortalin and/or Hsp60 after step (i), preferably at multiple time points after step (i), (iiB) comparing the expression level(s) obtained in step (iiA) to the expression level of mortalin and/or Hsp60 obtained before step (i), and (iiC) selecting, from among the test compounds, the compound that changes, preferably of at least 20%, preferably at least 30%, more preferably at least 50%, the expression level of mortalin and/or Hsp60 before and after step (i).

Preferably, the expression level is measured by ELISA in step (iiA).

Preferably, the compound of step (iiC) is the one which decreases or increases, preferably of at least 20%, preferably at least 30%, more preferably at least 50%, the expression level of mortalin and/or Hsp60 before and after step (i).

The determination of the expression level of mortalin and/or Hsp60 in the cells may be performed by any methods for detecting or measuring a specific protein or mRNA in a sample. Such methods may include, but are not limited to, an immunoassay, western blotting, or surface plasmon resonance (SPR) which can determine the amount of protein, and northern hybridization or quantitative real-time RT-PCR which can determine the amount of mRNA. Among these, immunoassays using anti-Hsp60 antibodies or anti-mortalin antibodies may be used for the screening method of the present invention because of their simplicity.

Among the immunoassays, enzyme-linked immunosorbent assay ("ELISA") may be preferable because the use of the enzymes which are linked to the detection agent may render the determination of the protein concentration easier and faster. Preferably, the expression level of mortalin and/or Hsp60 is determined by ELISA.

For example, in order to determine the amount of mortalin by using the ELISA, an anti-mortalin antibody is immobilized on a solid-phase substrate, and the cell lysate is subsequently applied onto the surface of the solid-phase substrate. A second anti-mortalin antibody that recognizes different epitopes from those recognized by the first antibody and that is labeled with an enzyme is then added and incubated so as to react with the captured mortalin. After being washed, the substrate of the enzyme is added to the surface of the solid-phase substrate for color development. The amount of mortalin can be determined by measuring the absorbance, etc. After the reaction between the antibodies immobilized on the solid-phase substrate and mortalin has taken place in the sample, the mortalin may be labeled by using non-labeled first antibodies that specifically bind to mortalin and then by using labeled secondary antibodies that specifically bind to the first antibodies.

In the case of peroxidase being used as an enzyme, the substrate may be, for example, 3,3'-diaminobenzidine (DAB), 3,3',5,5'-tetramethylbenzidine (TMB), or o-phenylenediamine (OPD). In the case of alkaline phosphatase being used as an enzyme, the substrate may be, for example, p-nitrophenylphosphate (NPP).

The term "solid-phase substrate" is not particularly limited and it may comprise, for example, a microtiter plate, a plate, a bead made of glass, metal or polymer etc., a nitrocellulose membrane, a nylon membrane, or a PVDF membrane. The antibodies for capturing the target proteins can be immobilized by any known method.

An anti-mortalin antibody may be a monoclonal antibody or a polyclonal antibody, both of which may be produced according to any known method. Monoclonal antibodies may be produced by immunizing a non-human mammal with mortalin or a fragment thereof, isolating the antibody-producing cells from the mammal, fusing the antibody-producing cells and myeloma cells to produce hybridoma, and purifying the antibodies produced by the hybridoma. Polyclonal antibodies may be obtained from the serum of an animal immunized with mortalin or its fragment. As the anti-mortalin antibodies, already exiting antibodies may be used.

Anti-Hsp60 antibodies may be obtained in the same manner as that explained above regarding the anti-mortalin antibodies.

The inventors of the present application have found that, with the increase of the mortalin or Hsp60 expression, tyrosinase activity increases and melanogenesis and pigmentation are facilitated, as shown in the later-described Examples. Accordingly, a substance that increases the expression level of mortalin and/or Hsp60 may be used as a protective agent against ultraviolet-induced skin damage or carcinogenesis, or a differentiating agent for skin cancers, through its ability to induce melanogenesis and pigmentation.

On the other hand, a substance that decreases the expression level of mortalin and/or Hsp60 may be used as a treatment agent for moles, dark spots that appear on aging skin or specific skin conditions, such as keloids or post-inflammatory hyperpigmentation. Such substance is also useful as a cosmetic agent for skin whitening. The term "whitening" as used herein, means making the skin color clearer, lighter or whiter, or decreasing dark spots or freckles on the skin.

The method of screening of the present invention may further comprise the step of inducing melanogenesis or pigmentation of the cells, before the step (i) of contacting the cells and the test compound. Such induction of melanogenesis or pigmentation may be performed by adding diacylglycerol (DAG), 1-oleoyl-2-acetyl-sn-glycero (OAG) or alpha-melanocyte-stimulating hormone (aMSH), for example to the culture medium of the cells.

The compound selected by the screening method of the present invention as a compound that decreases the expression level of mortalin and/or Hsp60 may be used as a cosmetic agent for skin whitening.

Figure 14:
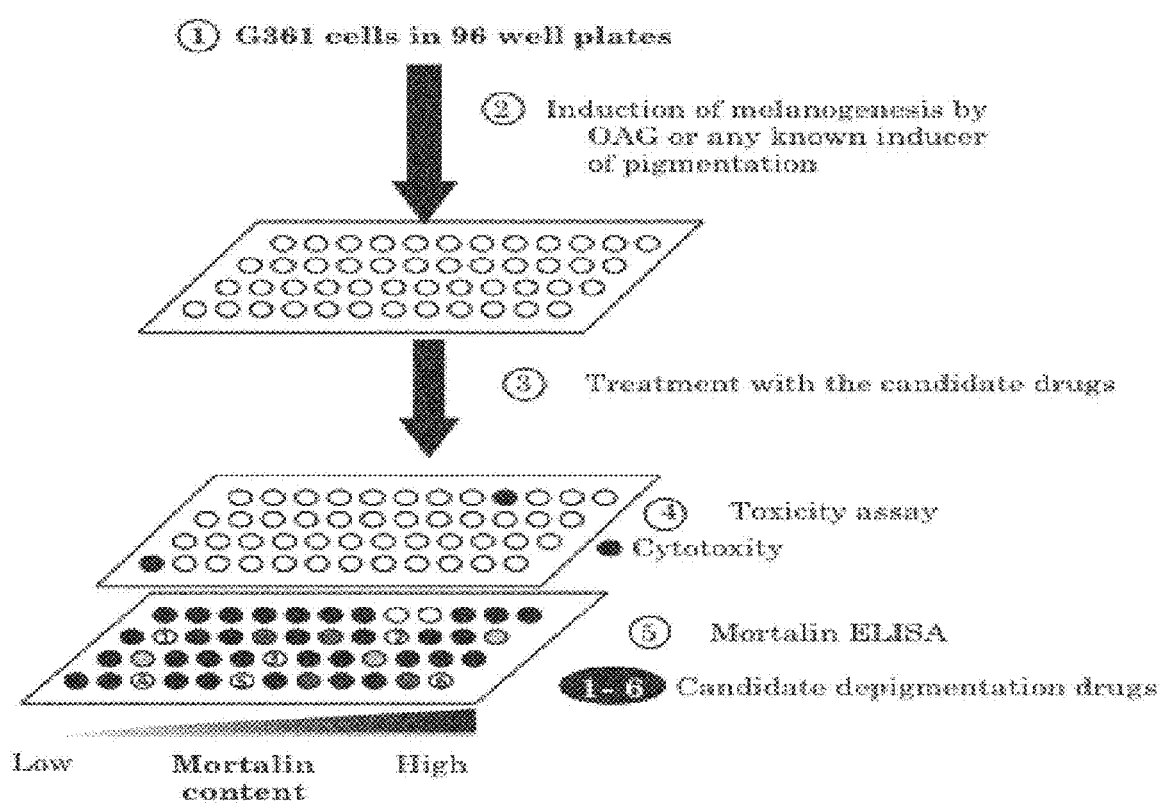
FIG. 14 shows a schematic example of the screening method of the present invention.

FIG. 14 shows a schematic example of the screening method of the present invention. As shown in the figure, G361 cells are prepared in a 96-well plate, and OAG is added in each well of the plate in order to induce pigmentation of G361 cells. Subsequently, a candidate compound is added to each well at appropriate concentrations and incubated. The conditions of the incubation can be appropriately determined by a person skilled in the art so that the reaction between the compound and the target takes place.

The screening method of the present invention may include a toxicity assay, by which the compounds having cytotoxicity can be removed from the candidates. The toxicity assay can be performed appropriately by a person skilled in the art. Lastly, the mortalin concentration of each well is determined by, for example, an ELISA assay.

Cosmetic Agent

The cosmetic agent of the present invention comprises a compound that decreases the expression level of mortalin and/or Hsp60 in the cells.

The term "cosmetic agent" as used herein, means, for example, a substance or composition intended to be applied to the human body for beautifying, promoting attractiveness, or altering appearance without affecting the body's structure or functions. The interpretation of such term may follow the definition made by the authorities of each country.

The form of the cosmetic agent of the present invention is not particularly limited, but it may comprise an aqueous system (e.g. skin lotion), an emulsifier system (e.g. emulsion or cream), a powder, an oil, a gel, an ointment, a water-oil two phase system (e.g. w/o emulsion or o/w emulsion), a water-oil-powder three phase system, and so on. The use or formulation is also not particularly limited, and the formulation may be any formulation used for a usual cosmetic agent, such as cream, emulsion, lotion, facial mask, lipstick, foundation, jelly, ointment, film, powder, and so on.

The method of manufacturing the cosmetic agent of the present invention is not particularly limited, and may comprise any known production methods of a cosmetic agent. For example, in the case of an emulsion or a cream, it may be produced by dissolving the selected compound in an aqueous phase component with an emulsifier, adding an oil phase component, and then mixing to emulsify the components.

Specific examples of the components of the cosmetic agents of the present invention include a powder component, a liquid oil, a solid fat, a wax, a hydrocarbon oil, a higher fatty acid, a higher alcohol (preferably an alcohol having 6 or more carbon atoms, and more preferably an alcohol having 10 or more carbon atoms), a synthetic ester oil, a silicone compound, a surfactant, a co-surfactant, a film forming agent, a gelling agent, a metal sequestering agent, a lower alcohol, a polyhydric alcohol or a derivative thereof, a monosaccharide, an oligosaccharide, an amino acid, a plant extract, an organic amine, a polymer emulsion, a cooling agent, a pH adjustor, a buffer, a perfume and water. Such components may be appropriately added if needed to produce a desired formulation form according to a conventional method.

There is no particular restriction on the content of these additives, insofar as the object of the present invention is not impaired, and the content may be appropriately selected depending on the form of the formulation or the product. These additives may be added in any steps. The timing of adding these additives may be appropriately selected depending upon the kinds of additives.

Examples of a powder component include inorganic powders, such as talc, kaolin, mica, sericite, white mica, gold mica, a synthetic mica, red mica, black mica, vermiculite, magnesium carbonate, calcium carbonate, aluminum silicate, barium silicate, calcium silicate, magnesium silicate, strontium silicate, a metal tungstate, silica, zeolite, barium sulfate, calcined calcium sulfate (calcined gypsum), calcium phosphate, fluorine apatite, hydroxyapatite, ceramic powder, metallic soap (e.g. zinc myristate, calcium palmitate and aluminum stearate) and boron nitride; organic powders, such as polyamide resin powder (nylon powder), polyethylene powder, polymethyl methacrylate powder, polystyrene powder, styrene/acrylic acid copolymer resin powder, benzoguanamine resin powder, polytetrafluoroethylene powder and cellulose powder; metal powder pigments, such as aluminum powder and copper powder; organic pigments, such as a zirconium-, barium-, and aluminum-lakes; and natural colors, such as chlorophyll and β-carotene.

Examples of a liquid oil include avocado oil, *camellia* oil, turtle oil, macadamia nut oil, corn oil, mink oil, olive oil, rapeseed oil, yolk oil, sesame oil, persic oil, wheat germ oil, *camellia* kissi oil, castor oil, linseed oil, safflower oil, cotton seed oil, *perilla* oil, soybean oil, peanut oil, tea seed oil, *Torreya* seed oil, rice bran oil, Chinese tung oil, Japanese tung oil, jojoba oil, germ oil, and triglycerin.

Examples of a solid fat include cacao butter, coconut oil, horse tallow, hardened coconut oil, palm oil, beef tallow, mutton tallow, hardened beef tallow, palm kernel oil, lard, cattle bone fat, Japan tallow kernel oil, hardened oil, neatsfoot oil, Japan tallow, and hardened castor oil.

Examples of a wax include bees wax, candelilla wax, cotton wax, carnauba wax, bayberry wax, Chinese insect wax, spermaceti, montan wax, bran wax, lanolin, kapok wax, acetylated lanolin, liquid lanolin, sugar cane wax, lanolin fatty acid isopropyl ester, hexyl laurate, reduction lanolin, jojoba wax, hard lanolin, shellac wax, POE lanolin alcohol ether, POE lanolin alcohol acetate, POE cholesterol ether, lanolin fatty acid polyethylene glycol, and POE hydrogenated lanolin alcohol ether.

Examples of hydrocarbon oil include liquid paraffin, ozokerite, squalane, pristane, paraffin, ceresin, squalene, vaseline, microcrystalline wax, and hydrogenated polydecene.

Examples of a higher fatty acid include lauric acid, myristic acid, palmitic acid, stearic acid, behenic acid, oleic acid, undecylenic acid, tall oil acid, isostearic acid, linoleic acid, linolenic acid, eicosapentaenoic acid (EPA), and docosahexaenoic acid (DHA). Examples of a higher alcohol include linear alcohols, such as lauryl alcohol, cetyl alcohol, stearyl alcohol, behenyl alcohol, myristyl alcohol, oleyl alcohol, and cetostearyl alcohol; branched alcohols, such as monostearyl glyceryl ether (batyl alcohol), 2-decyltetradecanol, lanolin alcohol, cholesterol, phytosterol, hexyldodecanol, isostearyl alcohol, and octyldodecanol.

Examples of a synthetic ester oil include tripropylene glycol dineopentanoate, isononyl isononanoate, isopropyl myristate, cetyl octanoate, octyldodecyl myristate, isopropyl palmitate, butyl stearate, hexyl laurate, myristyl myristate, decyl oleate, hexyldecyl dimethyloctanoate, cetyl lactate, myristyl lactate, acetylated lanolin, isocetyl stearate, isocetyl isostearate, cholesteryl 12-hydroxystearate, ethylene glycol di-2-ethylhexanoate, dipentaerythritol fatty acid ester, N-alkylglycol monoisostearate, neopentyl glycol dicaprylate, diisostearyl malate, glyceryl di-2-heptylundecanoate, trimethylolpropane tri-2-ethylhexanoate, trimethylolpropane triisostearate, pentaerythritol tetra-2-ethylhexanoate, glyceryl tri-2-ethylhexanoate, glyceryl trioctanoate, glyceryl triisopalmitate, trimethylolpropane triisostearate, cetyl 2-ethylhexanoate, 2-ethylhexyl palmitate, glyceryl trimyristate, glyceride tri-2-heptylundecanoate, castor oil fatty acid methyl ester, oleyl oleate, acetoglyceride, 2-heptylundecyl palmitate, diisobutyl adipate, N-lauroyl-L-glutamic acid-2-octyldodecyl ester, di-2-heptylundecyl adipate, ethyl laurate, di-2-ethylhexyl sebacate, 2-hexyldecyl myristate, 2-hexyldecyl palmitate, 2-hexyldecyl adipate, diisopropyl sebacate, 2-ethylhexyl succinate, and triethyl citrate.

Examples of a silicone compound include silicone oils, including linear polysiloxanes such as dimethylpolysiloxane, methylphenylpolysiloxane and diphenylpolysiloxane and cyclic polysiloxanes, such as octamethyl cyclotetrasiloxane, decamethyl cyclopentasiloxane and dodecamethyl cyclohexasiloxane; silicone resins forming a 3D net structure; silicone elastomers; various modified polysiloxanes, such as amino-modified polysiloxane, polyether-modified polysiloxane, alkyl-modified polysiloxane and fluorine-modified polysiloxane.

Examples of silicone elastomers include non-emulsifying organopolysiloxane elastomers or emulsifying organosiloxane elastomers. Examples of the non-emulsifying organopolysiloxane elastomers include dimethicone/vinyl dimethicone crosspolymers, lauryl dimethicone/vinyl dimethicone crosspolymers, and the like.

The dimethicone/vinyl dimethicone crosspolymers include products commercially available from DOW CORNING under the trade name of, for example, DC 9040 and DC 9045; products commercially available from GENERAL ELECTRIC under the trade name of SFE 839 and the Velvasil series products; products commercially available from SHIN ETSU under the trade name of, for example, KSG-15, KSG-16, and KSG-18 ([dimethicone/phenyl vinyl dimethicone crosspolymer]); and Gransil™ series products from GRANT INDUSTRIES.

The lauryl dimethicone/vinyl dimethicone crosspolymers include products commercially available from SHIN ETSU under the trade name of, for example, KSG-31, KSG-32, KSG-41, KSG-42, KSG-43, and KSG-44.

Examples of the emulsifying organosiloxane elastomers include polyalkoxylated silicone elastomers, polyglycerolated silicone elastomers, or the like.

The polyalkoxylated silicone elastomers include products commercially available from DOW CORNING under the trade name of, for example, DC9010 and DC9011; products commercially available from SHIN ETSU under the trade name of, for example, KSG-20, KSG-21, KSG-30, KSG-31, KSG-32, KSG-33, KSG-210, KSG-310, KSG-320, KSG-330, KSG-340, and X-226146.

The polyglycerolated silicone elastomers include products commercially available from SHIN ETSU under the trade name of, for example, KSG-710, KSG-810, KSG-820, KSG-830, KSG-840, KSG-31, KSG-32, KSG-41, KSG-42, KSG-43, and KSG-44.

Further, a silicone resin-hydrolyzed protein can be also used. Examples of a silicone resin-hydrolyzed protein include (hydrolyzed silk/PG-propyl methylsilanediol) crosspolymer and (trimethylsilyl hydrolyzed wheat protein/PG-propyl methylsilanediol)crosspolymer. A commercially available product may be used as a silicone resin-hydrolyzed protein. Examples of such a commercially available product include products of Seiwa Kasei Co., Ltd. under the trade names of PROTESIL FN, PROTESIL LH, and PROTESIL GLH.

Examples of a surfactant include a lipophilic nonionic surfactant and a hydrophilic nonionic surfactant.

Examples of a lipophilic nonionic surfactant include a sorbitan fatty acid ester, such as sorbitan monooleate, sorbitan monoisostearate, sorbitan monolaurate, sorbitan monopalmitate, sorbitan monostearate, sorbitan sesquioleate, sorbitan trioleate, diglycerol sorbitan penta-2-ethylhexylate and diglycerol sorbitan tetra-2-ethylhexylate; a glyceryl polyglyceryl fatty acid, such as glyceryl monocotton seed oil fatty acid, glyceryl monoerucate, glyceryl sesquioleate, glyceryl monostearate, glyceryl α,α'-oleate pyroglutamate, and glyceryl monostearate malate; a propylene glycol fatty acid ester such as monostearate propylene glycol; a hydrogenated castor oil derivative; and a glycerin alkyl ether.

Examples of a nonionic surfactant oil include a POE-sorbitan fatty acid ester, such as POE-sorbitan monooleate, POE-sorbitan monostearate, POE-sorbitan monooleate and POE-sorbitan tetraoleate; a POE sorbitol fatty acid ester, such as POE-sorbitol monolaurate, POE-sorbitol monooleate, POE-sorbitol pentaoleate, POE-sorbitol monostearate; a POE-glycerin fatty acid ester, such as POE-glycerin monooleate, POE-glycerin monostearate, POE-glycerin monoisostearate and POE-glycerin triisostearate; a POE-fatty acid ester, such as POE-monooleate, POE-distearate, POE-monodioleate and ethylene glycol distearate; a POE-alkyl ether, such as POE-lauryl ether, POE-oleyl ether, POE-stearyl ether, POE-behenyl ether, POE-2-octyldodecyl ether and POE-cholestanol ether; a Pluronic type surfactant (e.g. Pluronic); a POE-POP-alkyl ether, such as POE-POP-cetyl ether, POE-POP-2-decyltetradecyl ether, POE-POP-monobutyl ether, POE-POP-hydrogenated lanolin and POE-POP-glycerin ether.

Examples of co-surfactants include higher alcohols. Among them, linear fatty alcohols such as lauryl alcohol, cetyl alcohol, stearyl alcohol, behenyl alcohol, myristyl alcohol, oleyl alcohol, cetostearyl alcohol, and the like, are preferable. Cetyl alcohol is further preferable.

Examples of a gelling agents include nonionic polymers, cationic polymers, as well as anionic polymers and amphoteric polymers with an anionic group, such as gum Arabic, carrageenan, karaya gum, Tragacanth gum, *Pyrus cydonia* seed (marmelo), casein, gelatin, sodium pectate, sodium alginate, xanthan gum, pectin, fucoidan, galactomannan, curdlan, gellan gum, Fucogel® (a fucose-rich polysaccharide), collagen, sodium hyaluronate, Alcasealan® (a polysaccharide produced by *alcaligenes*), propylene glycol alginate, and dialkyl dimethyl ammonium cellulose sulfate).

Examples of a metal sequestering agent include 1-hydroxyethane-1,1-diphosphonic acid; 1-hydroxyethane-1,1-diphosphonic acid tetrasodium salt; disodium edetate; trisodium edetate; tetrasodium edetate; sodium citrate; sodium polyphosphate; sodium metaphosphate; gluconic acid; phosphoric acid; citric acid; ascorbic acid; succinic acid; edetic acid; and trisodium ethylenediamine hydroxyethyl triacetate.

Examples of a lower alcohol include ethanol, propanol, isopropanol, isobutyl alcohol, and t-butyl alcohol.

Examples of a polyhydric alcohol or a derivative thereof include a dihydric alcohol, such as ethylene glycol, propylene glycol, pentylene glycol, trimethylene glycol, 1,2-butylene glycol, 1,3-butylene glycol, tetramethylene glycol, 2,3-butyleneglycol, pentamethylene glycol, 2-butene-1,4-diol, hexylene glycol and octylene glycol; a trihydric alcohol, such as glycerin and trimethylolpropane; a tetrahydric alcohol such as pentaerythritol (e.g. 1,2,6-hexanetriol); a pentahydric alcohol such as xylitol; a hexahydric alcohol, such as sorbitol and mannitol; a polyhydric alcohol polymer, such as diethylene glycol, dipropylene glycol, triethylene glycol, polypropylene glycol and tetraethylene glycol; a dihydric alcohol alkyl ether, such as ethylene glycol monomethyl ether and ethylene glycol monoethyl ether; a dihydric alcohol alkyl ether, such as diethylene glycol monomethyl ether, diethylene glycol monoethyl ether and diethylene glycol monobutyl ether; a dihydric alcohol ether ester, such as ethylene glycol monomethyl ether acetate and ethylene glycol monoethyl ether acetate; a glyceryl monoalkyl ether, such as chimyl alcohol, selachyl alcohol and batyl alcohol; and a sugar alcohol, such as sorbitol, maltitol, maltotriose, mannitol, sucrose, erythritol, glucose, fructose, starch sugar, maltose, xylitose, and a reduced alcohol of a starch sugar.

Examples of a monosaccharide include a triose, such as D-glyceryl aldehyde and dihydroxyacetone; a tetrose, such as D-erythrose, D-erythrulose, D-threose and erythritol; a pentose, such as L-arabinose, D-xylose, L-lyxose, D-arabinose, D-ribose, D-ribulose, D-xylulose and L-xylulose; a hexose, such as D-glucose, D-talose, D-psicose, D-galactose, D-fructose, L-galactose, L-mannose and D-tagatose; a heptose, such as aldoheptose and heprose; an octose such as octurose; a deoxy sugar, such as 2-deoxy-D-ribose, 6-deoxy-L-galactose and 6-deoxy-L-mannose; an amino sugar, such as D-glucosamine, D-galactosamine, sialic acid, amino uronic acid and muramic acid; a uronic acid, such as D-glucuronic acid, D-mannuronic acid, L-guluronic acid, D-galacturonic acid and L-iduronic acid.

Examples of an oligosaccharide include sucrose, lactose, maltose, trehalose, cellobiose, gentiobiose, umbilicin, raffinose, gentianose, maltotriose, melezitose, planteose, unbelliferose, stachyose, and verbascose.

Examples of an amino acid include a neutral amino acid, such as threonine and cysteine; and a basic amino acid such as hydroxylysine. Further, as an amino acid derivative, such as sodium acyl sarcosinate (sodium lauroyl sarcosinate), acyl glutamate, sodium acyl β-alanine, glutathione, and pyrrolidone carboxylic acid may be exemplified.

Examples of an organic amine include monoethanolamine, diethanolamine, triethanolamine, morpholine, triisopropanolamine, 2-amino-2-methyl-1,3-propanediol, and 2-amino-2-methyl-1-propanol.

Examples of a polymer emulsion include an acrylic resin emulsion, a poly(ethyl acrylate) emulsion, an acrylic resin solution, a poly(alkyl acrylate) emulsion, a poly(vinyl acetate) emulsion, and a natural rubber latex.

These additives are mentioned in International Cosmetic Ingredient Dictionary and Handbook, 9th Edition, 2002, published by the Cosmetic, Toiletry and Fragrance Association, which can be referred to.

The composition for external use according to the present invention may further contain various active agents such as vitamins, antioxidants, moisturizing agents, blood flow promoters, antibacterial agents, cell (skin) activating agents, emollients, anti-aging agents, anti-pollution agents, keratolytic agents, astringents, anti-inflammatory agents, whitening agents, and sunscreens.

Examples of a vitamin include vitamins A, B1, B2, B6, C and E and derivatives thereof, pantothenic acid and derivatives thereof and biotin.

Examples of antioxidants include ascorbic acid and its derivatives such as ascorbyl palmitate, ascorbyl tetraisopalmitate, ascorbyl glucoside, magnesium ascorbyl phosphate, sodium ascorbyl phosphate and ascorbyl sorbate; tocopherol and its derivatives, such as tocopheryl acetate, tocopheryl sorbate, and other esters of tocopherol; dibutyl hydroxytoluene (BHT) and butylated hydroxyanisole (BHA); gallic acid ester; phosphoric acid; citric acid; maleic acid; malonic acid; succinic acid; fumaric acid; cephalin; a hexametaphosphate; phytic acid; ethylenediaminetetraacetic acid; and plant extracts, for instance from *Chondrus cripsus, Rhodiola, Thermus thermophilus*, mate leaf, oak wood, kayu rapet bark, sakura leaves and ylang ylang leaves.

Examples of moisturizing agent include polyethylene glycol; propylene glycol; dipropylene glycol; glycerin; 1,3-butylene glycol; xylitol; sorbitol; maltitol; mucopolysaccharides, such as chondroitin sulfuric acid; hyaluronic acid; sodium hyaluronate, sodium acetylated hyaluronate, mucoitinsulfuric acid; caronic acid; atelo-collagen; cholesteryl-12-hydroxystearate; bile salt; a main component of NMF (natural moisturizing factor), such as a pyrrolidone carboxylic acid salt, and a lactic acid salt; amino acids such as urea, cysteine and serine; short-chain soluble collagen; a diglycerin (EO) PO addition product; homo- and copolymers of 2-methacryloyloxyethylphosphorylcholine commercially available from NOF under the name of, for example, Lipidure HM and Lipidure PBM; panthenol; allantoin; PEG/PPG/Polybutylene Glycol-8/5/3 Glycerin commercially available from NOF under the trade name of Wilbride S 753; Trimethylglycine commercially available from Asahi KASEI Chemicals under the trade name of AMINOCOAT; and various plant extracts such as *Castanea sativa* extracts, hydrolyzed hazelnut proteins, *Polianthes tuberosa* polysaccharides, *Argania spinosa* kernel oil, and an extract of pearl containing conchiolin commercially available from Maruzen Pharmaceuticals under the trade name of Pearl Extract™.

Examples of emollients include glyceryl polymethacrylate, methyl gluceth-20, and the like.

Examples of anti-aging agents include acyl amino acids (specifically, products commercially available from SEDERMA under the trade name of Maxilip, Matrixyl 3000 or Biopeptide CL, or product commercially available from SEPPIC under the trade name of Sepilift); *Pisum sativum* extracts; hydrolyzed soy proteins; methylsilanol mannuronate; hydrolyzed *cucurbita pepo* seedcake; *Scenedesmus* extract; and the like. Examples of anti-pollution agents include *Moringa pterygosperma* seed extracts (specifically, product commercially available from LSN under the trade name of Purisoft); Shea butter extract (specifically, products commercially available from SILAB under the trade name of Detoxyl, a blend of ivy extract, phytic acid, sunflower seed extract (for example, product commercially available from SEDERMA under the trade name of OSMOPUR), and the like.

Examples of keratolytic agents include α-hydroxy acids (specifically, glycolic, lactic, citric, malic, mandelic or tartaric acid) and β-hydroxy acids (specifically, salicylic acid), and their esters (specifically, C12-13 alkyl lactate), plant extracts containing these hydroxy acids (specifically, *Hibiscus sabdriffa* extracts), and the like.

Examples of astringents include *hamamelis* extracts, and the like.

Examples of anti-inflammatory agents include bisabolol, allantoin, tranexamic acid, zinc oxide, sulfur oxide and its derivatives, chondroitin sulfate, glycyrrhizinic acid and its derivatives (for example, glycyrrhizinates).

The composition for external use according to the present invention may contain at least one whitening agent to block the synthesis of structural proteins such as the melanocyte-specific glycoprotein Pme117 involved in the mechanism of melanogenesis (stage I). Example of such a whitening agent may include the ferulic acid-containing cytovector (water, glycol, lecithin, ferulic acid, hydroxyethylcellulose) commercially available from BASF under the trade name Cytovector™.

Furthermore, if necessary, the composition for external use according to the present invention may contain at least one peptide as described in the patent application WO2009/010356.

Furthermore, if necessary, the composition for external use according to the present invention may include a whitening agent having an inhibition effect on melanin synthesis and/or an inhibition effect on nanophthalmia-related transcription factor (MITF) expression and/or an anti-tyrosinase activity and/or an inhibition effect on endothelin-1 synthesis. Examples of such a whitening agent may include *Glycyrrhiza glabra* extract commercially available from Maruzen Pharmaceuticals under the trade name Licorice Extract™.

Furthermore, if necessary, the composition for external use according to the present invention may include whitening agents having an antioxidant effect as well, such as vitamin C compounds, which include ascorbate salts, ascorbyl esters of fatty acids or of sorbic acid, and other ascorbic acid derivatives. Specific examples include ascorbyl phosphates (magnesium ascorbyl phosphate, sodium ascorbyl phosphate, and the like), saccharide esters of ascorbic acid (ascorbyl-2-glucoside, 2-O-α-D-glucopyranosyl L-ascorbate, or 6-O-β-D-galactopyranosyl L-ascorbate, and the like). Active agents of this type are commercially available from DKSH under the trade name of Ascorbyl Glucoside™.

Furthermore, if necessary, the composition for external use according to the present invention may include other whitening agents. Examples of the other whitening agents include pigmentation inhibiting agents such as plant extracts (*Narcissus tazetta* extracts), arbutin, kojic acid, ellagic acid, cysteine, 4-thioresorcin, resorcinol or rucinol or their derivatives, glycyrrhizinic acid, hydroquinone-β-glucoside, and the like.

Furthermore, if necessary, the composition for external use according to the present invention may also include organic and/or inorganic sunscreens.

Examples of the organic sunscreens may include dibenzoylmethane derivatives such as butyl methoxydibenzoylmethane (product commercially available from HOFFMANN LA ROCHE under the trade name of Parsol 1789); cinnamic acid derivatives such as ethylhexyl methoxycinnamate (product commercially available from HOFFMANN LA ROCHE under the trade name of Parsol MCX), salicylates, para-aminobenzoic acids; β-β'-diphenylacrylate derivatives; benzophenone derivatives; benzylidenecamphor derivatives such as terephtalylidene dicamphor sulphonic acid; phenylbenzimidazole derivatives; triazine derivatives; phenylbenzotriazole derivatives; anthranilic derivatives, and the like, all of which may be coated or encapsulated.

Examples of the inorganic sunscreens may include nanopigments formed from coated or uncoated metal oxides, such as, for example, titanium oxide, iron oxide, zinc oxide, zirconium oxide or cerium oxide nanopigments; which are all UV photoprotective agents well known per se.

The formulation form of the composition for external use of the present invention is arbitrarily selectable, and may be a liquid or semi-liquid or solid composition of any type, including solutions, emulsions, gels, but also powders optionally including a water and/or oil phase therein.

Further, the product form of these compositions for external use is also arbitrarily selectable, and the composition is applicable to facial cosmetics, such as a facial cleanser, a face lotion, an essence liquid, a milky lotion, a cream and a pack; makeup cosmetics, such as a foundation, a lipstick and an eye shadow; body makeup products; hair care cosmetics; oral care toiletries; perfumeries; cleansers; and ointments.

Pharmaceutical Composition

A compound that decreases the expression level of mortalin and/or Hsp60 selected by the screening method of the present invention may be used in a pharmaceutical composition used for the treatment of the diseases or conditions caused by excess melanin, including moles, keloids, or hyperpigmentation.

A compound that increases the expression level of mortalin and/or Hsp60 selected by the screening method of the present invention may be used in a pharmaceutical composition used for the treatment or prevention of cancers or for the differentiation of skin cancers.

Said pharmaceutical composition may have an action on the mitochondrial function and/or on oxidative stress of the targeted cells.

The pharmaceutical composition of the present invention may be formulated according to any known method. Examples of the formulation may include oral agents such as granules, fine grain agents, powdered medicines, tablets, encapsulated formulations, liquid medicines, syrups, chewable formulations, lozenges, sublingual formulations; topical products such as ointments, gels, creams, patches; injectable formulations; inhalations; ophthalmic solutions; and suppositories.

The amount of the selected compound in each formulation may be appropriately determined by a person skilled in the art.

The present invention also provides a pharmaceutical composition comprising an expression vector comprising mortalin and/or Hsp60 gene(s), or a mortalin protein and/or Hsp60 protein.

Such pharmaceutical composition may increase mortalin and/or Hsp60 directly in the body of a patient and induce melanogenesis or pigmentation. Accordingly, the pharmaceutical composition may be used as a preventive for UV-induced skin damage or skin cancer, or as a differentiating agent for skin cancer.

This pharmaceutical composition may also be prepared by the methods described above.

Manipulation Method of Cultured Skin Color

The present invention also provides a method for controlling melanogenesis or pigmentation in cultured skin cells, comprising differentiating stem cells into skin cells in vitro, and regulating the amount of mortalin and/or Hsp60 in the cultured skin cells.

By this method, the color of cultured skin can be controlled. For example, a cultured skin may be produced by differentiating stem cells such as iPS cells or ES cells, and its color may be controlled in accordance with, for example, the skin color of the patient to whom the cultured skin is transplanted.

The regulation of the amount of mortalin and/or Hsp60 can be performed by, for example, adding the compound selected by the screening method of the present invention to the culture medium of the stem cells. When a compound that increases the expression level of mortalin and/or Hsp60 is added to the culture medium, the color of the cultured skin could be changed towards being brown or black. On the other hand, when a compound that decreases the expression level of mortalin and/or Hsp60 is added to the culture medium, the color of the cultured skin could be changed towards being white.

The regulation of the amount of mortalin and/or Hsp60 may be performed by adding mortalin and/or Hsp60 directly to the medium, or transforming the stem cells with an expression vector containing mortalin and/or Hsp60 gene(s).

The present invention will hereinafter be described in detail based on Examples, but it should be noted that the invention is not limited by them.

Methods employed in the following Examples will next be described.

Example 1

Material and Methods

Cell Culture, Treatments and Transfections

The human melanoma G361 were bought from Cell Resource Center for Biomedical Research, Tohoku University, Japan and were cultured in DMEM (Dulbecco's Modified Eagle's Medium, Invitrogen) supplemented with 10% fetal bovine serum in a humidified incubator (37° C. and 5% $CO_2$). Human primary melanocytes from the light and dark skin donors were bought from ScienCell Research Laboratories and were cultured in the recommended melanocyte growth medium. Cells were transfected with the expression plasmids coding for either mortalin or HSP60 protein using Fugene (Roche) as per recommended protocol. Typically 3-5 μg of plasmid DNA was used for 6 cms culture dish at 70-80% confluency. Cells were incubated with the plasmids for 48 hrs after which cells were harvested and examined for the expression indicated genes by protocols as described below. For shRNA transfections, Oligofectamine™ Transfection Reagent (Life Technologies™) was used as per manufacturer's instructions. Transfected cells were incubated with medium supplemented with puromycin (1 ug/ml) for 24-48 hrs and were then processed for assays as described below.

Drug Treatments

Cells were treated with pigment inducers such as, Di-acyl glycerol (OAG, 20 ug/ml), 3-Isobutyl-1-methylxanthine (IBMX –100 uM)(Merck Millipore), PD98059 (20 ug/ml) (Life Technologies) and hydrogen peroxide (150-300 µM) for 48 hrs.

The following drugs were used:
18=*Cananga* leaf extract
39=Ume flower extract
46=Oolong tea extract commercialized by Maruzen (INCI name: WATER & BUTYLENE GLYCOL & *CAMELLIA SINENSIS* LEAF EXTRACT).

The *Cananga* leaf extract was prepared as follows: the extract of *Cananga odorata* was obtained by extraction of crushed leaves with ethyl alcohol, decoloration of the mixture with activated carbon, filtration, recovery of the filtrate and evaporation of the ethyl alcohol, take-up via propylene glycol and filtration in order to obtain a viscous liquid extract.

The Ume flower extract was obtained by extraction with a 50% ethanol solution, then mixing with a 30% ethanol solution to naturally precipitate, filtration to remove precipitation and final mixture with a 50% butylene glycol solution to obtain the liquid extract.

Vitamin C Treatment

Cells were treated with Di-acyl glycerol (OAG, 20 µg/ml) for 24 h followed by recovery either in the normal medium as described below or Vitamin C (0.1-0.3 mM) for 24 to 48 hrs.

TXC (Cetyl Tranexamate Hydrochloride Salt) Treatment

Cells were treated with TXC as follows.

G361 cells were cultured overnight and allowed to adhere to the surface well after which they were treated with TXC supplemented medium or OAG as described below followed by recovery in the TXC medium at doses indicated in the data figs.

Knockdown of Hsp60 and Mortalin

Construction of Mortalin shRNA Vectors

Mortalin targeting shRNA expression plasmid was generated with U6 promoter vector as described (Miyagishi et al (2004) J Gene Med, 6: 715-723 and Yoo et al, (2010). J. Gene Medicine 12, 586-595). Three target sites used for mortalin were #007-GCAACAAGCTGAAAGAAGA (SEQ ID NO:1); #008-GCCAGAAGGACAACATATG (SEQ ID NO:2) and #009-GAATGAGGCTAGACCTTTA (SEQ ID NO:3). Typically, in order to generate mortalin targeting shRNA, the DNA fragments for the expression of shRNA targeting human mortalin were generated by annealing the sense oligonucleotide 5'-gatcccGCAACAAGCT-GAAAGAAGAttcaagagaTCTTCTTTCAGCTTGTT-GCttttttgga aa-3' (SEQ ID NO:4) and its cognate antisense oligonucleotide 5'-agcttttccaaaaaaGCAACAAGCT-GAAAGAAGAttcaagagaTCTTCTTTCAGCTTGTTG Cgg-3' (SEQ ID NO:5). The 19-nucleotide mortalin target sequences are indicated in uppercase letters, whereas the 9-nucleotide hairpin and the sequences necessary for the directional cloning are depicted in lowercase letters.

Construction of HSP60 shRNA Vector

HSP60 targeting shRNA expression vector was generated as described above. Two target sites used were—5' GTGAGATGAGGAGCCAGTACC 3' (SEQ ID NO:6) and 5' TTCAAGCATTAAGGCTCGGGC 3' (SEQ ID NO:7).

Construction of HSP60 and Mortalin Overexpression Vectors

For overexpression of Hsp60 and mortalin, retrovirus expression system was used. cDNA encoding full-length HSP60 or mortalin protein was cloned into the BamHI site of the vector as described (Wadhwa et al 2006 International J Cancer, 118: 2973-2980). For production of retroviruses, Plat-E, an ecotropic murine leukemia virus (MuLV)-packaging cell line was transfected with the pVPack-GP (expression gal and pol) and pVPack VSVG (expressing env) vectors (Stratagene, Calif.) and either pCXneo retroviral vector or pCX4neo/mortalin using FuGENE6 (Boehringer Mannheim). After 48 h, culture supernatants were collected, filtered through 0.45 µm filters and used as viral stocks for infection. MCF7 cells ($2 \times 10^5$/well in 6-well dishes) were treated with 8 µg/ml polybrene for 1 h at 370° C., following which cells were infected with 200 µl of filtered viral stock for 1 h. The plates were tilted after every 15 min to spread viral particles over the cells. After 1 h, 2 ml of DMEM was added to the culture to dilute the viral stock and the plates were incubated at 370 C for a further 48 h. Cells were selected in medium containing G418 (1 mg/ml) until stable expressing cell lines were obtained.

Tyrosinase ELISA

Cells (Approximately 10000 cells/well) were plated in 96 well Nunc-Immuno maxisorp plates. At about 70% confluency, cells were transfected with shRNA plasmids (100 ng/well) as described above. After 24 hrs post-transfection, the cells were selected in puromycin-supplemented medium and were then processed for tyrosinase ELISA as described below. Cells were washed with PBS twice and were lysed in RIPA lysis buffer (Santa Cruz Biotechnology). Protein concentrations of the lysates were determined (Pierce BCA Protein Assay kit, Thermo Scientific) and the samples were diluted to 1 ug/ul concentration in coating buffer (0.1 M Sodium bicarbonate, 0.02% Sodium Azide pH-9.6). 5 µg of the protein sample was added to each well in a final volume of 100 µl of the coating buffer. The plates were gently shaken for 10 min and were then securely sealed and left for 2 hrs at room temperature. The solution was discarded and the plates were washed with washing buffer (PBS-0.5% TWEEN® 20, which is polysorbate 20) for 5 min. Blocking buffer (200 ul) was added to each well and the plates were incubated for 2 hours at room temperature followed by washings with the Washing buffer twice (3 min each). Anti-tyrosinase antibody (50 µl, 5 µg/ml in the blocking buffer) was added to each well and the plated were sealed and kept at room temperature for 1-2 hrs followed by washings with the washing buffer (3×10 min). The plates were incubated with the secondary antibody (Alkaline phosphatase, AP-Goat anti Rabbit IgG) for 1 hr and were then washed with the washing buffer for 3-5 times. The 100 µl of the substrate for AP (Nitrophenyl Phosphate, Disodium Salt, PNPP) was added to each well. Plates were again sealed and left for 30 min followed by measuring the absorbance at 405 nm that represented the quantitative estimation of tyrosinase expression.

Melanin Content

Cells were plated in 96 well plates and allowed to attach well to the surface of the plate for 24 hours followed by transfections and treatments as described above and indicated in the figure legends. Cells were washed with PBS. Potassium hydroxide (KOH-0.85 N, 100 µl) was added to each. The plates were shaken gently in dark for overnight.

Absorbance of the pigment was measured at 405 nm. Melanin content was calculated by using standard purified melanin (Sigma).

Immunostaining

Cells were cultured and treated on glass coverslips placed in 12-well culture dish. At the end of the treatment as described above, coverslips were washed with cold phosphate-buffered saline (PBS) and the cells were fixed with pre-chilled methanol:acetone (1:1 v/v) mixture for 5-10 min. Fixed cells were washed with PBS, permeabilized with 0.2% TRITON™ X-100 (4-(1,1,3,3-Tetramethylbutyl)phenyl-polyethylene glycol) in PBS for 10 min, and blocked with 2% bovine serum albumin (BSA) in PBS for 20 min. Cells were stained with anti-mortalin, anti-HSP60, anti-tyrosinase and anti-melanosome antibodies. Immunostaining was visualized by secondary staining with Alexa-488 or Alexa-594 conjugated antibodies (Molecular probes). After three to four washings with 0.2% TRITON™ X-100 in PBS (PBST), cells were overlaid with Fluoromount (Difco). The cells were examined with Carl Zeiss microscope with epifluorescence optics.

Western Blotting

Cells were grown and treated in 6-well plates. After transfections or drug treatments as described above, the cells were lysed with RIPA lysis buffer. Cell lysate (30 µg) was resolved on SDS-PAGE followed by transfer onto a nitrocellulose membrane (Millipore) using a semidry transfer blotter. Immunoassays were done with anti-mortalin, anti-HSP70 and anti-tyrosinase antibodies. The immunocomplexes formed were visualized with horseradish peroxidase-conjugated anti-rabbit/mouse immunoglobulin G. The bands were detected by LAS 3000 mini (FujiFilm).

Results

Establishment of Assay for Screening of Genes Involved in Melanogenesis

FIG. 1 shows the results of immunohistochemistry analysis of melanosome induction in control and OAG-treated primary melanocytes from a white skin donor (A) and human melanoma cells G361 (B). PI staining was used as a nuclear staining in order to spot the cells. In both primary melanocytes from a white skin donor and human melanoma cells G361, melanosome production was induced by OAG.

Figure 2:
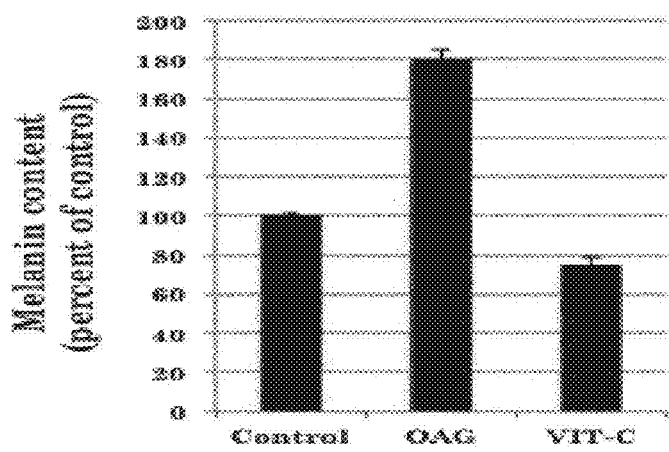
FIG. 2 shows the melanin content in G361 treated with OAG (center) or with OAG and Vitamin C (right).

FIG. 2 shows the results of calculation of melanin content. Increase in melanin content was observed in the cells treated with OAG. Vitamin C (a positive control for depigmentation) treatment caused reduction in the OAG-induced melanin content.

Figure 3:
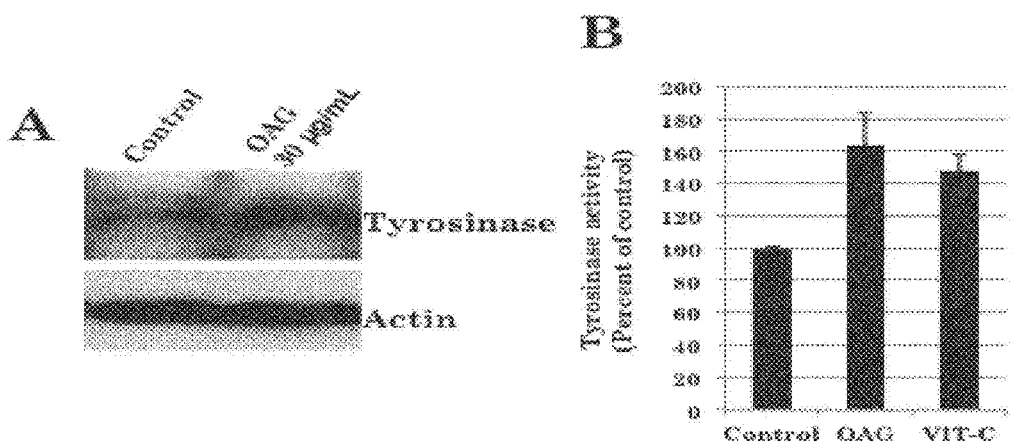
FIG. 3 shows the results of western blotting of tyrosinase (A) and tyrosinase activity assay (B).

FIG. 3 shows the results of Western blotting of tyrosinase (A) and tyrosinase ELISA assay (B). In OAG-treated G361 cells, increase in tyrosinase expression and activity was observed. Vitamin-C treatment caused decrease in the OAG-induced tyrosinase. These results supported that the present experimental system appropriately indicates the effect of the present invention. As a result of shRNA screening, mortalin and Hsp60 genes were selected and subjected to validation for their role in melanogenesis.

Validation of Selected Genes for their Role in Melanogenesis.

Figure 4:
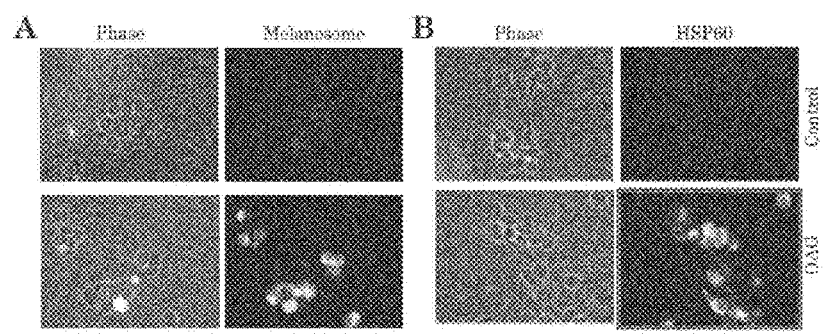
FIG. 4 shows the results of immunostaining of melanosome and Hsp60 upon induction of melanogenesis by OAG.

FIG. 4 shows the results of immunostaining of melanosome and Hsp60 upon induction of melanogenesis by OAG. Induction of melanogenesis by OAG resulted in upregulation of Hsp60.

Figure 5:
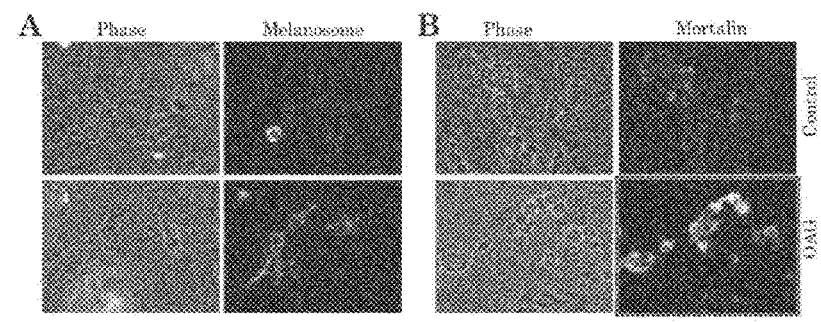
FIG. 5 shows the results of immunostaining of melanosome and mortalin upon induction of melanogenesis by OAG.

FIG. 5 shows the results of immunostaining of melanosome and mortalin upon induction of melanogenesis by OAG. Induction of melanogenesis by OAG resulted in upregulation of mortalin.

Figure 6:
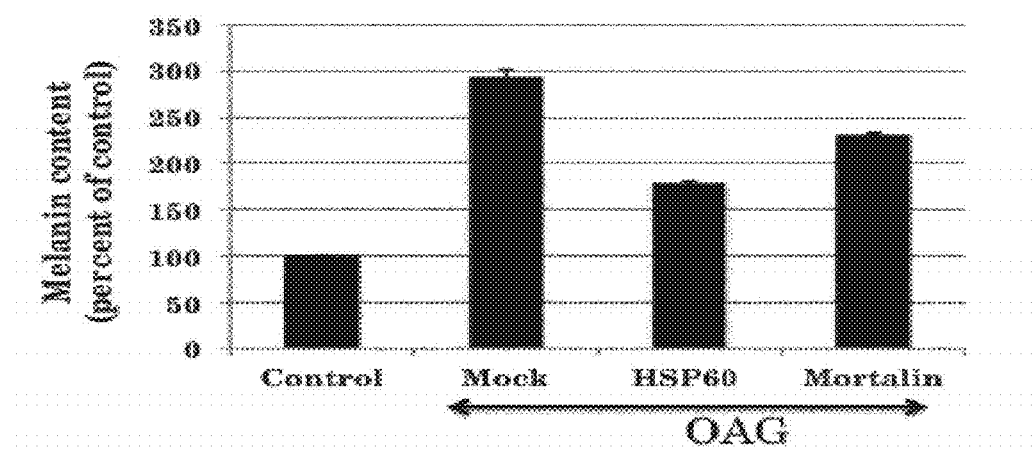
FIG. 6 shows the melanin content upon knockdown of Hsp60 or mortalin in OAG-treated G361 cells.

FIG. 6 shows the melanin content upon knockdown of Hsp60 and mortalin in OAG-treated G361 cells. Knockdown of Hsp60 or mortalin caused reduction in the OAG-induced increase in melanin in G361 cells.

Figure 7:
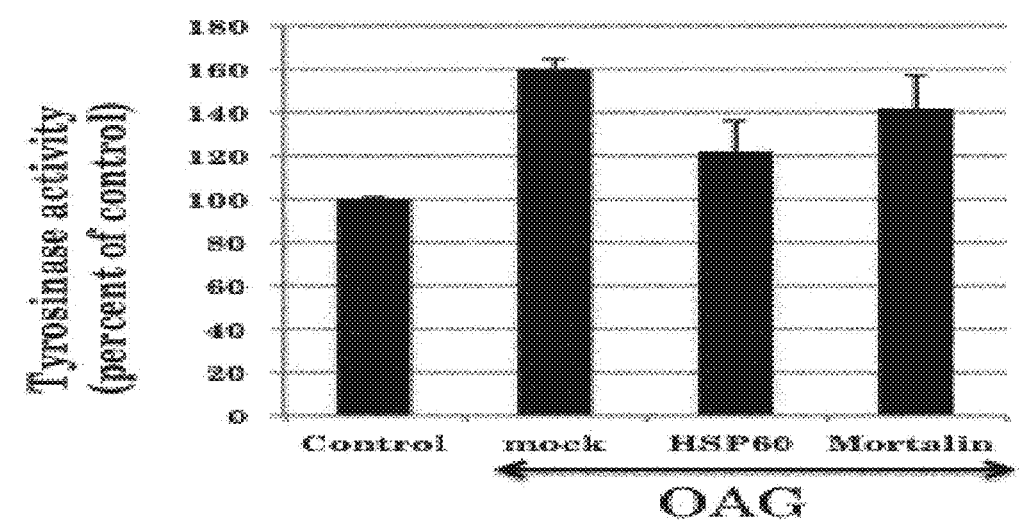
FIG. 7 shows the tyrosinase activity upon knockdown of Hsp60 or mortalin in OAG-treated G361 cells.

FIG. 7 shows the tyrosinase activity upon knockdown of Hsp60 or mortalin in OAG-treated G361 cells. Knockdown of Hsp60 and mortalin caused reduction in the OAG-induced increase in tyrosinase activity in G361 cells.

Figure 8:
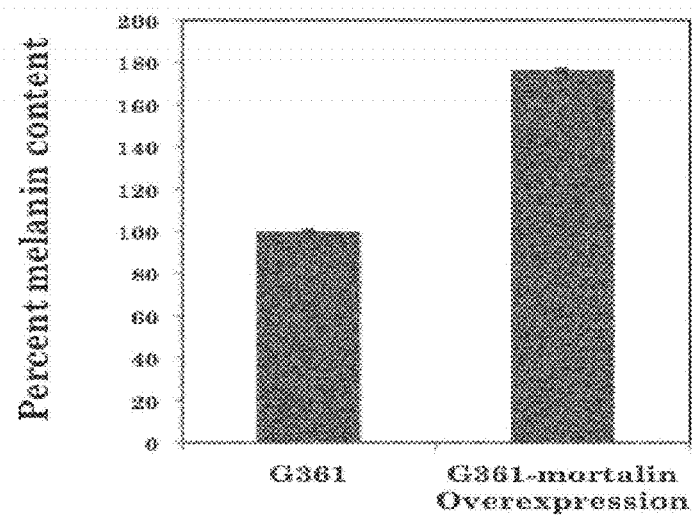
FIG. 8 shows the melanin content upon mortalin over-expression in G361 cells.

FIG. 8 shows the melanin content when mortalin was over-expressed in G361 cells. Over-expression of mortalin resulted in increase in the endogenous melanin content.

Figure 9:
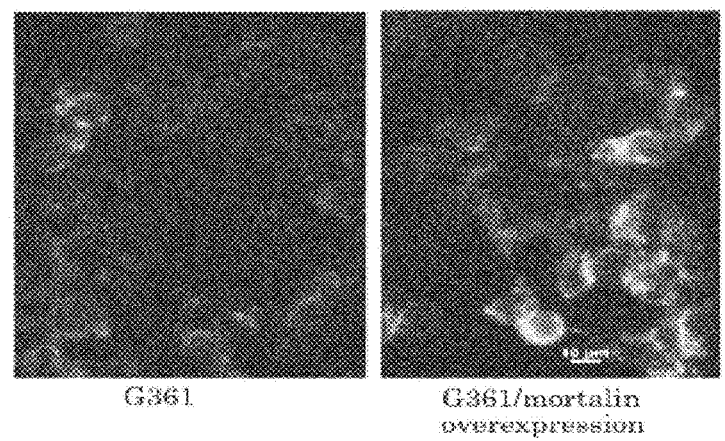
FIG. 9 shows the melanosome staining upon mortalin over-expression in G361 cells.

FIG. 9 shows the melanosome staining when mortalin was over-expressed in G361 cells. Over-expression of mortalin resulted in increase in the endogenous melanosome.

Figure 10:
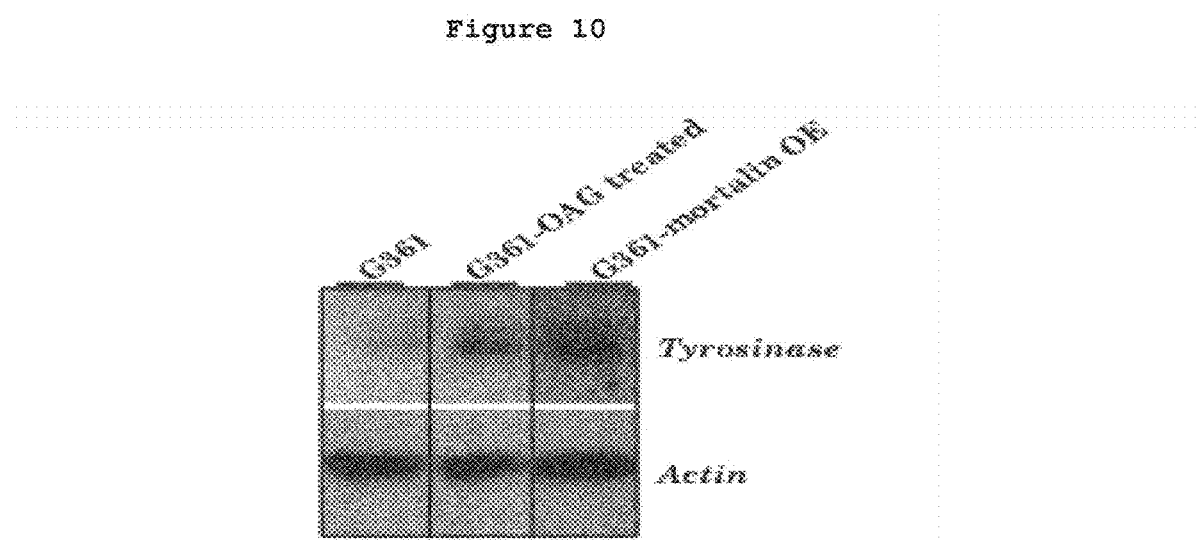
FIG. 10 shows the tyrosinase activity upon mortalin over-expression in G361 cells.

FIG. 10 shows the tyrosinase activity when mortalin was over-expressed in G361 cells. Over-expression of mortalin resulted in increase in the tyrosinase activity.

Figure 15:
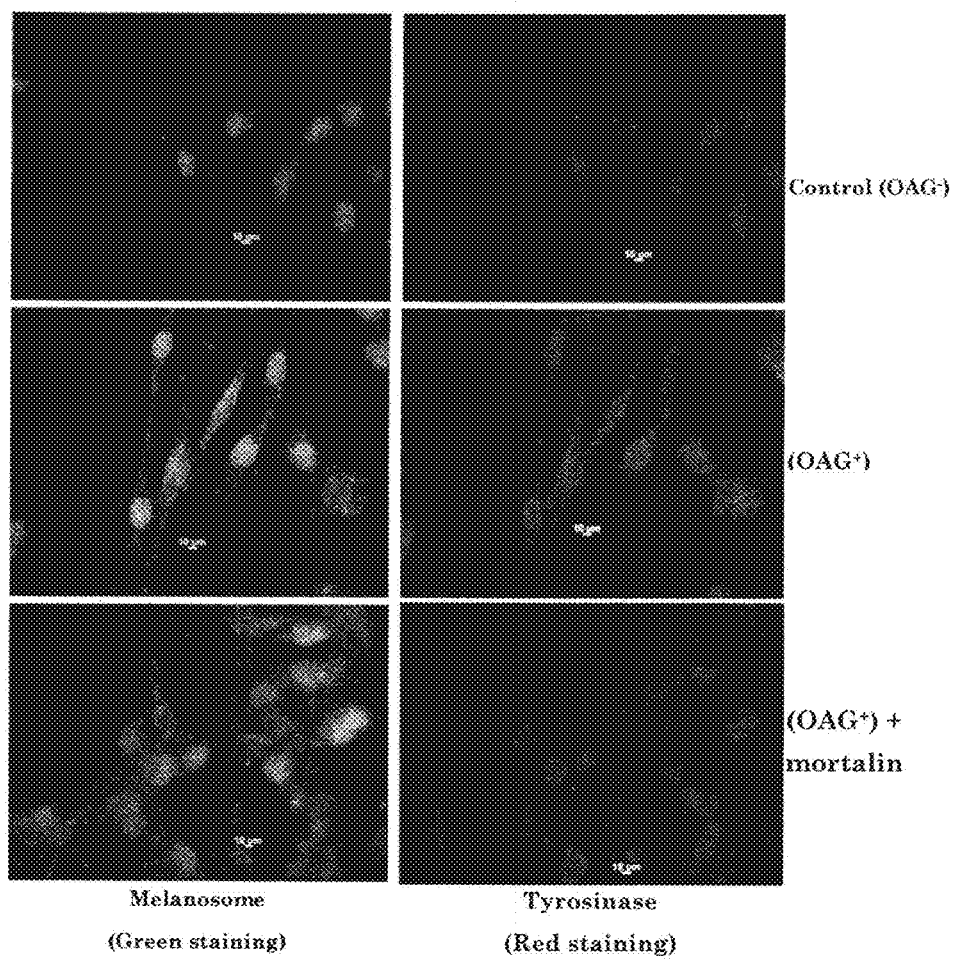
FIG. 15 shows G361 cells transfected with mortalin specific shRNA and then subjected to OAG-induced melanogenesis.

FIG. 15 shows G361 cells transfected with mortalin specific shRNA and then subjected to OAG-induced melanogenesis. As shown, shRNA-mediated knockdown of mortalin resulted in reduced OAG-induced melanosome as well as tyrosinase cytostaining.

The above results show that intracellular content of Hsp60 and mortalin is positively correlated with tyrosinase activity and production of melanin and melanosome. Therefore, it is confirmed that Hsp60 and mortalin can be used as indicator of melanogenesis.

Validation of the Usefulness of the Screening Method of the Present Invention

Figure 11:
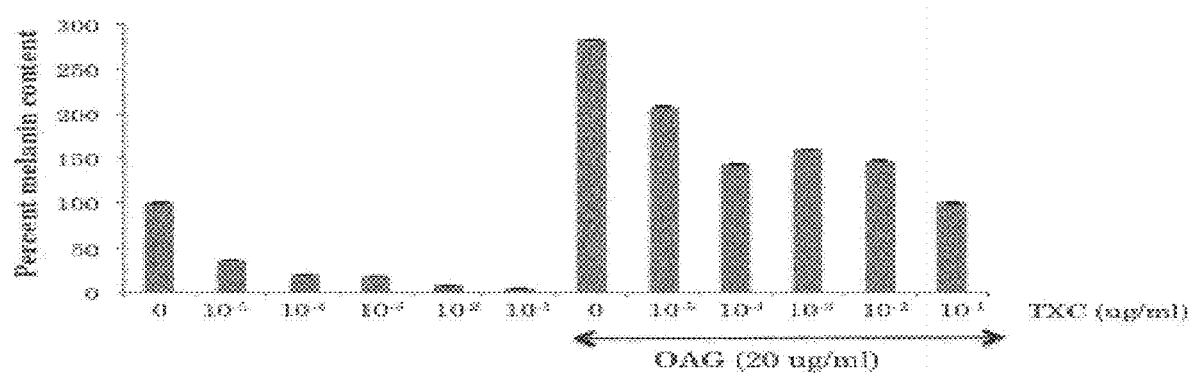
FIG. 11 shows the melanin content in OAG-treated or OAG-untreated G361 cells after TXC treatment at various concentrations.

FIG. 11 shows melanin content in OAG-treated or OAG-untreated G361 cell after TXC treatment at various concentrations. TXC treatment caused reduction in endogenous melanin and OAG-induced melanin in the cells.

Figure 12:
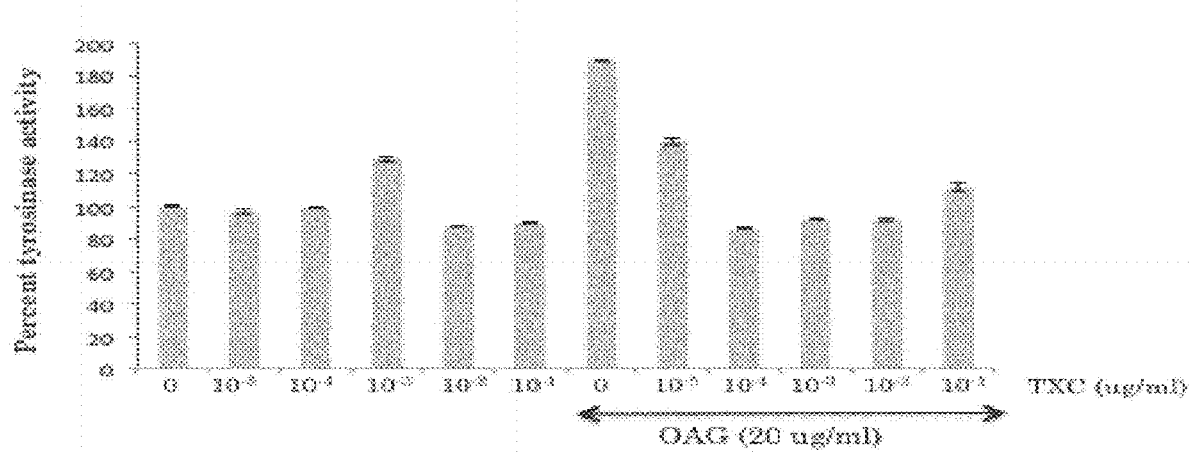
FIG. 12 shows tyrosinase activity in OAG-treated or OAG-untreated G361 cells after TXC treatment at various concentrations.

FIG. 12 shows tyrosinase activity in OAG-treated or OAG-untreated G361 cells after TXC treatment at various concentrations. TXC treatment caused reduction in OAG-induced tyrosinase activity in the cells.

Figure 13:
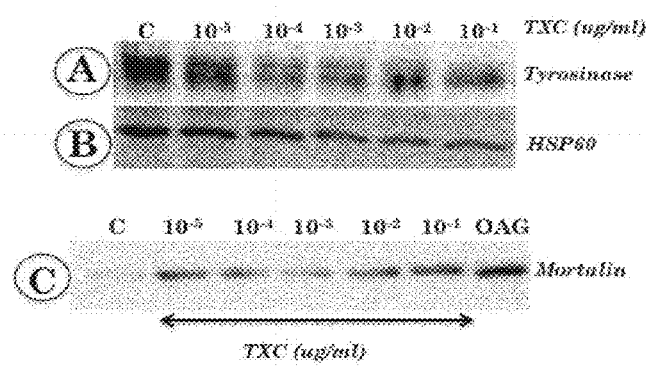
FIG. 13 shows tyrosinase, Mortalin and Hsp60 expressions in TXC-treated G361 cells.
    A) Reduction in tyrosinase expression in G361 cells treated with TXC.
    B) Reduction in HSP60 expression in G361 cells treated with TXC.
    C) Increase in mortalin expression in cells treated with OAG and its decrease when the cells were recovered in TXC-supplemented medium.

FIG. 13 shows tyrosinase and Hsp60 expressions in TXC-treated G361 cells, and OAG-induced expression of Mortalin in TXC-treated G361 cells. TXC treatment caused reduction in endogenous expressions of tyrosinase and Hsp60, and in endogenous and OAG-induced expression of Mortalin in G361 cells.

Figure 16:
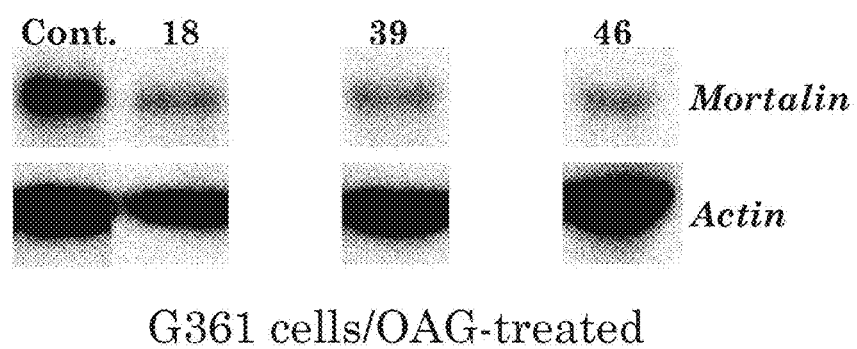
In FIGS. 16 to 19, the following numbers are attributed to the following drugs:
    18=*Cananga* leaf extract
    39=Ume flower extract
    46=Oolong tea extract commercialized by Maruzen

FIG. 16 shows G361 cells treated with OAG (30 µg/ml) followed by their recovery in the absence (control) or presence of either of the 3 drugs (indicated by numbers), selected on the basis of the screening method, shown in FIG. 14. As shown, the drug treated cells exhibited decrease in OAG-induced mortalin as detected by immunoblotting. Actin was used as an internal loading control.

Figure 17:
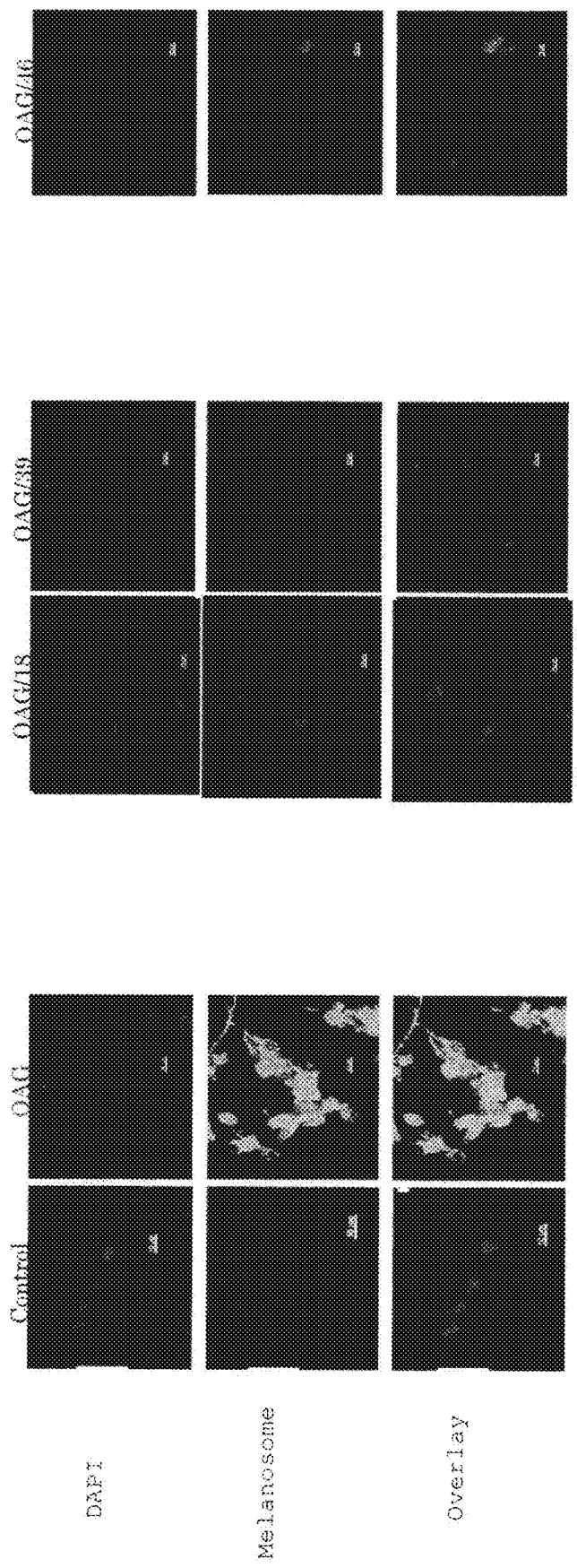

FIG. 17 shows G361 cells treated with OAG followed by their recovery in the absence (control) or presence of either of the 3 drugs (indicated by numbers), selected on the basis of the screening method, shown in FIG. 14. Drug-treated melanoma cells showed reduction in OAG (30 µg/ml)-induced melanosome staining.

Figure 18:
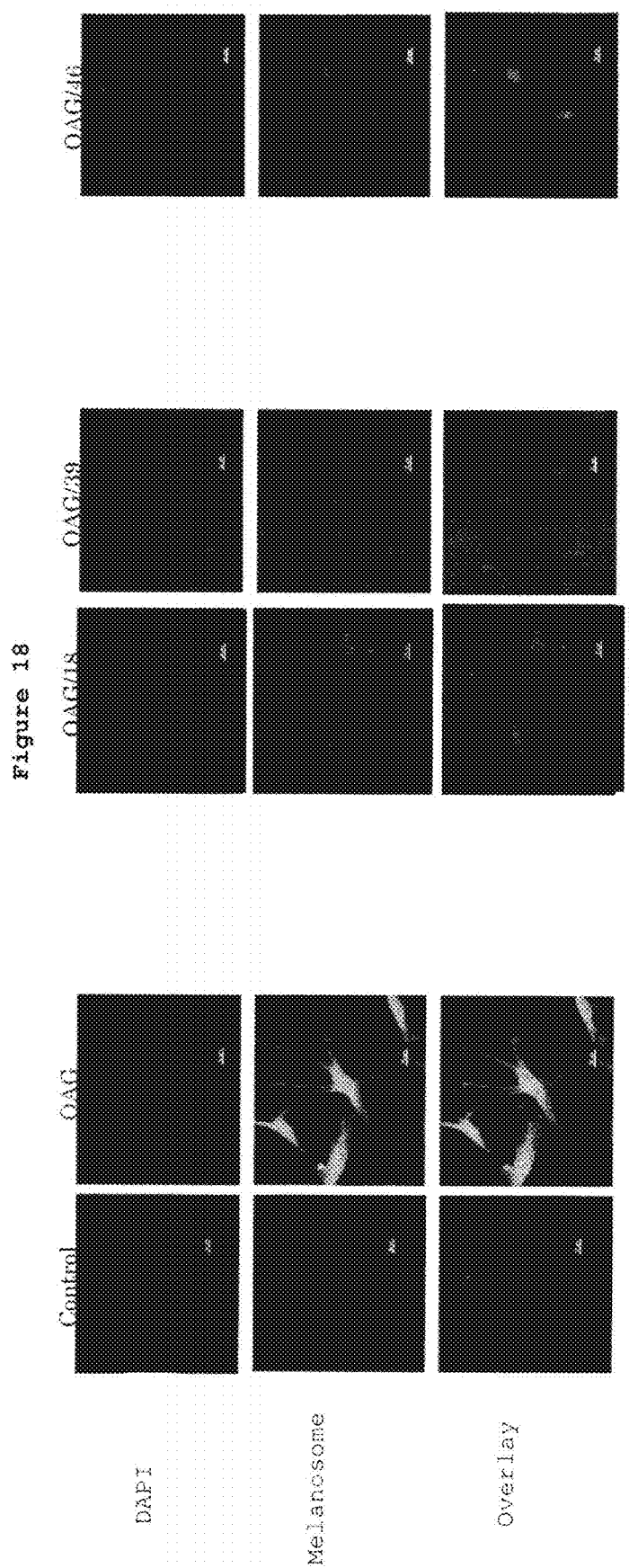

FIG. 18 shows primary melanocytes derived from human white skin treated with OAG (15 µg/ml). As shown, melanin induction was recorded by staining the melanosomes (green). Cells treated with either of the 3 (18, 39 and 46) indicated drugs showed reduction in melanosome staining.

Figure 19:
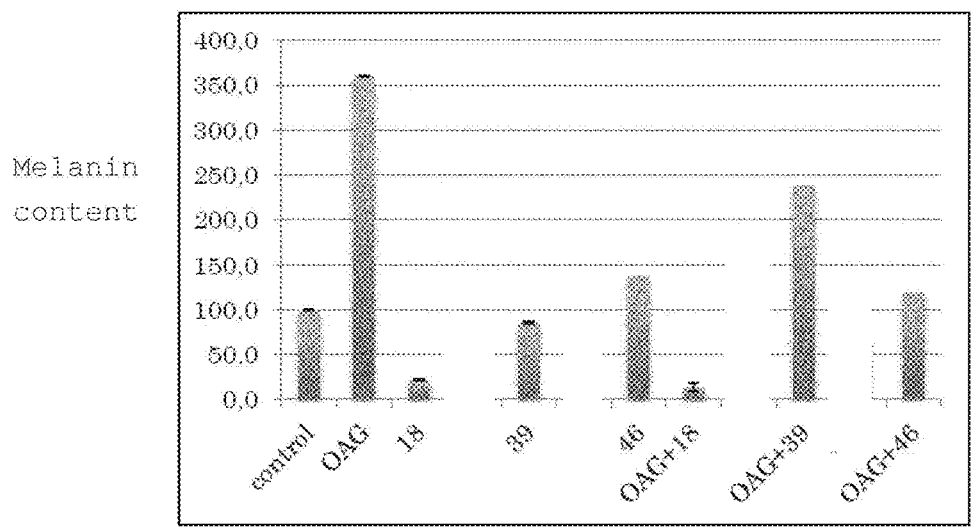

FIG. 19 shows human white skin-derived primary melanocytes treated with OAG (15 µg/ml). The increase in melanin content declined when cells were treated with either of the 3 (18, 39 and 46) drugs. Endogenous level of melanin was reduced in the presence of drugs 18 and 39. OAG-induced increase in melanin was reduced by all the 3 drugs.

The above results show that TXC treatment that decreases the expressions of Tyrosinase, Mortalin, and Hsp60 induces reduction in endogenous or OAG-induced melanin in the G361 cells. Based on these results, it is understood that the compound selected by the screening method of the present invention, as it decreases the expression level of Mortalin and/or Hsp60, will be useful for depigmentation, whitening or inhibition of melanogenesis, like TXC.

Example 2: Cosmetic Compositions

The following compositions can be prepared in a manner conventional to those skilled in the art:

a) O/W Emulsion Serum

| INCI name | % (W/W) |
| --- | --- |
| Water | QSP 100 |
| Glycol | 6% |
| Preservatives | 0.9% |
| Alcohol | 10% |
| dimethicone | 2 |
| hydrogenated polydecene | 3 |
| isononyl isononanoate | 2 |
| steareth-21 | 1 |
| steareth-2 | 2 |
| glyceryl stearate | 1.5 |
| PEG-150 distearate | 0.4 |
| sodium acrylate/sodium acryloyldimethyltaurate copolymer & isohexadecane & polysorbate 80 | 1 |
| acrylates/C10-30 alkyl acrylate crosspolymer | 0.5 |
| sodium polyacrylate | 0.4 |
| xanthan gum | 0.15 |
| Ume flower extract | 1% |
| TXC | 3 |
| Licorice | 0.02 |
| Hydrolyzed conchiolin protein | 0.1 |
| Ascorbyl glucoside | 2 |
| Ethyl ascorbic acid | 1 |
| Sodium hyaluronate | 0.05 |
| Perfume | | b) O/W Emulsion Serum

| INCI name | % (W/W) |
| --- | --- |
| Water | QSP 100 |
| Glycol | 6% |
| Preservatives | 0.9% |
| Alcohol | 10% |
| dimethicone | 2 |
| Isopropyl Lauroyl Sarcosinate | 2 |
| isononyl isononanoate | 2 |
| Sorbitan Stearate | 0.2 |
| Polysorbate 6 | 0.3 |
| glyceryl stearate | 0.1 |
| Sorbeth-40 Tetraoleate | 0.5 |
| hydroxyethyl cellulose | 0.4 |
| carrageenan | 0.5 |
| sodium alginate | 0.4 |
| xanthan gum | 0.15 |
| Cananga leaf extract | 1% |
| TXC | 3 |
| Licorice | 0.02 |
| Hydrolyzed conchiolin protein | 0.1 |
| Ascorbyl glucoside | 2 |
| Ethyl ascorbic acid | 1 |
| Sodium hyaluronate | 0.05 |
| Perfume | |

The invention claimed is:

1. An in vitro method of screening for candidate cosmetic compounds for regulating melanogenesis or pigmentation, comprising the steps of:
   (i) determining by enzyme-linked immunosorbent assay ("ELISA"), in a sample of cells expressing mortalin and/or heat shock protein 60 (Hsp60), the expression level of mortalin and/or Hsp60;
   (ii) bringing a test compound into contact with said sample of cells expressing mortalin and/or Hsp60 in vitro;
   (iii) determining by ELISA, in said cells from step (ii), the expression level of mortalin and/or Hsp60;
   (iv) identifying a change in the expression level of mortalin and/or Hsp60 measured in step (iii) as compared to the expression level of mortalin and/or Hsp60 measured in step (i), and
   (v) selecting said candidate cosmetic compound for possible incorporation into a cosmetic composition for regulating melanogenesis or pigmentation.

2. The method according to claim 1 wherein the change in step (iv) is an increase or decrease in the expression level of mortalin and/or Hsp60 of at least 20%.

3. The method according to claim 1, wherein the cells expressing mortalin and/or Hsp60 are chosen from human melanoma cells and melanocytes.

* * * * *